US011723614B2

(12) United States Patent
Hu

(10) Patent No.: US 11,723,614 B2
(45) Date of Patent: Aug. 15, 2023

(54) DYNAMIC 3-D ANATOMICAL MAPPING AND VISUALIZATION

(71) Applicant: Jerry Chi Hu, Soldotna, AK (US)

(72) Inventor: Jerry Chi Hu, Soldotna, AK (US)

( * ) Notice: Subject to any disclaimer, the term of this patent is extended or adjusted under 35 U.S.C. 154(b) by 167 days.

(21) Appl. No.: 16/844,482

(22) Filed: Apr. 9, 2020

(65) Prior Publication Data

US 2021/0196217 A1 Jul. 1, 2021

Related U.S. Application Data

(60) Provisional application No. 62/955,657, filed on Dec. 31, 2019.

(51) Int. Cl.
*A61B 6/00* (2006.01)
*A61B 6/03* (2006.01)

(52) U.S. Cl.
CPC .............. *A61B 6/466* (2013.01); *A61B 6/032* (2013.01); *A61B 6/4085* (2013.01); *A61B 6/463* (2013.01); *A61B 6/469* (2013.01); *A61B 6/50* (2013.01); *A61B 6/5205* (2013.01); *A61B 2562/0247* (2013.01)

(58) Field of Classification Search
CPC ............................ A61B 6/4085; A61B 8/4416
See application file for complete search history.

(56) References Cited

U.S. PATENT DOCUMENTS

| 5,835,693 A * | 11/1998 | Lynch .................... B25J 9/1605 |
| | | 345/473 |
| 8,798,346 B2 | 8/2014 | Cizek |
| 2004/0019285 A1 * | 1/2004 | Eigler ..................... A61B 5/03 |
| | | 600/488 |

(Continued)

FOREIGN PATENT DOCUMENTS

| WO | 2007087333 A2 | 8/2007 |
| WO | 2011/014804 | 2/2011 |

OTHER PUBLICATIONS

Yu, C. et al. "Acoustic Rhinometry and Acoustic Pharyngometry in the Modeling of Upper Airway Based on CT Scan," 2010 4th International Conference on Bioinformatics and Biomedical Engineering, 2010, pp. 1-4 (Year: 2010).*

(Continued)

*Primary Examiner* — Boniface Ngathi N
*Assistant Examiner* — Milton Truong

(57) ABSTRACT

A system and method for providing dynamic 3-D anatomical visualizations generates a 3D visualization of a patient's airway that may be dynamically transformed to characterize changes to the airway (e.g., as the patient breathes, when patient performs a Mueller's manoeuvre, and/or in response to mandibular repositioning). The 3D visualization is generated based on an integration of static 3D image data and acoustic reflection measurements of the airway determined and provided by an acoustic reflection measurement device. The movements or changes to the region of interest may be determined based on real-time dynamic readings taken by the acoustic reflection measurement device, and the 3D visualization may be transformed in real-time or near real-time stream based on the dynamic readings. The transformation of the 3D visualization provides an animated visualization of the airway.

18 Claims, 14 Drawing Sheets

(56) References Cited

U.S. PATENT DOCUMENTS

| | | | |
|---|---|---|---|
| 2010/0316278 A1* | 12/2010 | Hartung | A61B 8/08 |
| | | | 382/131 |
| 2011/0066058 A1 | 3/2011 | Singh | |
| 2011/0240015 A1* | 10/2011 | Nikander | A61M 15/00 |
| | | | 128/200.14 |
| 2014/0275994 A1 | 9/2014 | Liu et al. | |
| 2017/0236327 A1* | 8/2017 | Somasundaram | G06T 19/20 |
| | | | 345/419 |
| 2020/0138518 A1* | 5/2020 | Lang | A61B 5/05 |

OTHER PUBLICATIONS

Tsolakis, I.A. et al. "When static meets dynamic: Comparing cone-beam computed tomography and acoustic reflection for upper airway analysis". Am J Orthod Dentofacial Orthop. 2016, 150(4):643-650 (Year: 2016).*

Huang, J.F. et al. "Assessment of Upper-Airway Configuration in Obstructive Sleep Apnea Syndrome With Computed Tomography Imaging During Müller Maneuver". Respir Care. 2016, 61(12): 1651-1658. (Year: 2016).*

Jung, D.G. et al. "Predictive Value of Kushida Index and Acoustic Pharyngometry for the Evaluation of Upper Airway in Subjects With or Without Obstructive Sleep Apnea". J Korean Med Sci 2004; 19: 662-7 (Year: 2004).*

Schwab, Richard J. et al. "Dynamic imaging of the upper airway in normal subjects". J Appl Physiol Apr. 1993;74(4):1504-14 (Year: 1993).*

Di Carlo G, et al. "A new simple three-dimensional method to characterize upper airway in orthognathic surgery patient." Dentomaxillofac Radiol. 46(8):20170042. (2017) (Year: 2017).*

Al-Saleh, M.A.Q. et al. "MRI and CBCT image registration of temporomandibular joint: a systematic review". Journal of Otolaryngology—Head and Neck Surgery (2016) 45:30 (Year: 2016).*

"Employing Acoustic Pharyngometry to Improve Efficacy of Oral Airway Therapy Device When Mandibular Advancement is Ineffective", Date: Mar. 2, 2016, 12 Pages, Dental Sleep Practice, Scottsdale, AZ, USA.

Matteo Gelardi, et al, "Acoustic pharyngometry: clinical and instrumental correlations in sleep disorders", Brazilian Journel of Otorhnolaryngology, Date: Mar./Apr. 2007, vol. 73, Issue 2, pp. 257-265, Sao Paulo, Brazil.

Raphael Richert, et al., "Intraoral Scanner Technologies: A Review to Make a Successful Impression",Journeal of Healthcare Engineering, Date: Sep. 5, 2017, vol. 2017, 9 Pages, London, UK.

Bradley M. Hemminger et al., "Assessment of Real-Time 3D Visualization for Cardiothoracic Diagnostic Evaluatior and Surgery Planning", Journal of Digital Imaging, Date Jun. 2005, vol. 18, No. 2, USA.

University of California San Diego Health Sciences Surgeon Plans Procedure on Himself with 3D Visualization, https://www.mpo-mag.com/contents/view_videos/2017-03-10/surgeon-plans-procedure-on-himself-with-3d-visualization. Date: Mar. 10, 2017, MPO; Medical Product Outsourcing, USA.

3-D Visualization and Augmented Reality for Surgery; https://innovations.clevelandclinic.org/Programs/Top-10-Medical-Innovations/Top-10-for-2017/8-3-D-Visualization-and-Augmented-Reality-for-Sur, Cleveland Clinic Innovations, 2016 USA.

Ranjith Kumar Sicakumar, et al., "Ultrasonopraphy as a novel airway assessment tool for preoperative dynamic airway evaluation in an anticipated difficult airway", Indian Journal of Anaesthesia, pp. 3, vol. 61, Issue 12, Dec. 2017, India.

PCT International Search Report and Written Opinion in International Application PCT/US2020/067188, dated Apr. 27, 2021, 8 pages.

Douros, Loannis, et al., "Towards a method of dynamic vocal tract shapes generation by combining static 3D and dynamic 2D Mri speech data", In: INTERSPEECH 2019-20th Annual Conference of the International Speech Communication Association. Jul. 12, 2019, abstract, chapters 2.1, 3.2-3 4.

Zhu, Yinghua, et al., "Dynamic 3-D visualization of vocal tract shaping during speech", IEEE transactions on medical imaging, 2012, vol. 32, Issue 5, pp. 838-848.

* cited by examiner

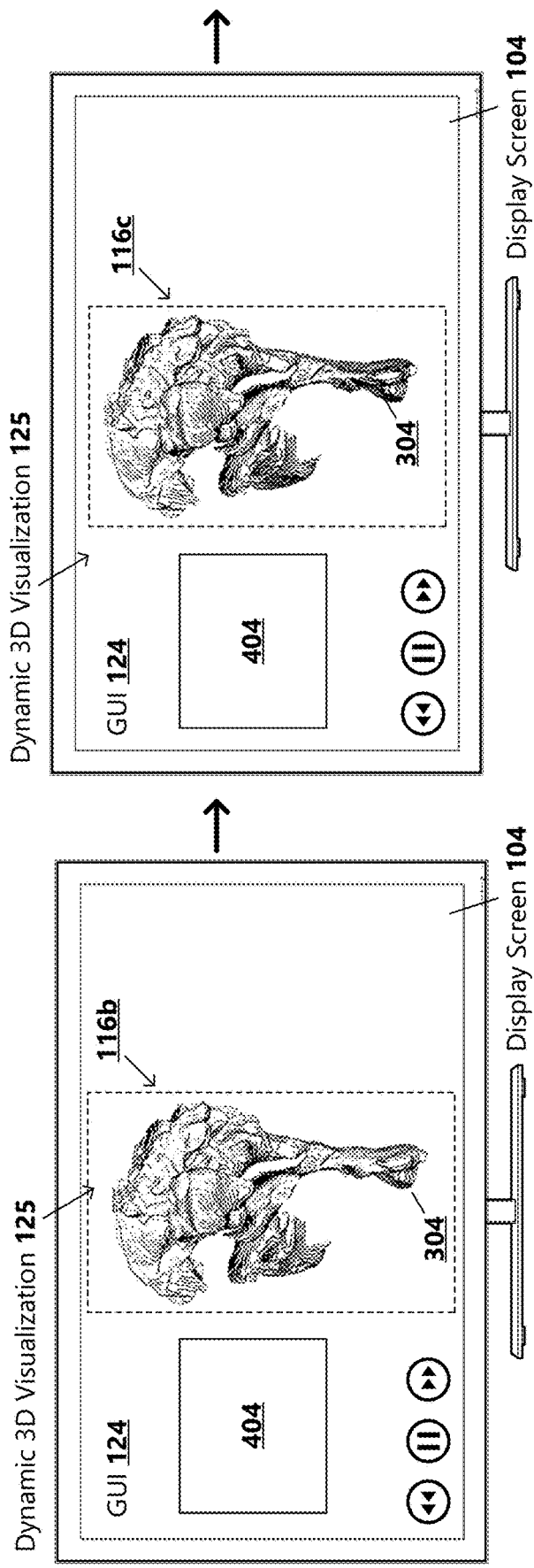

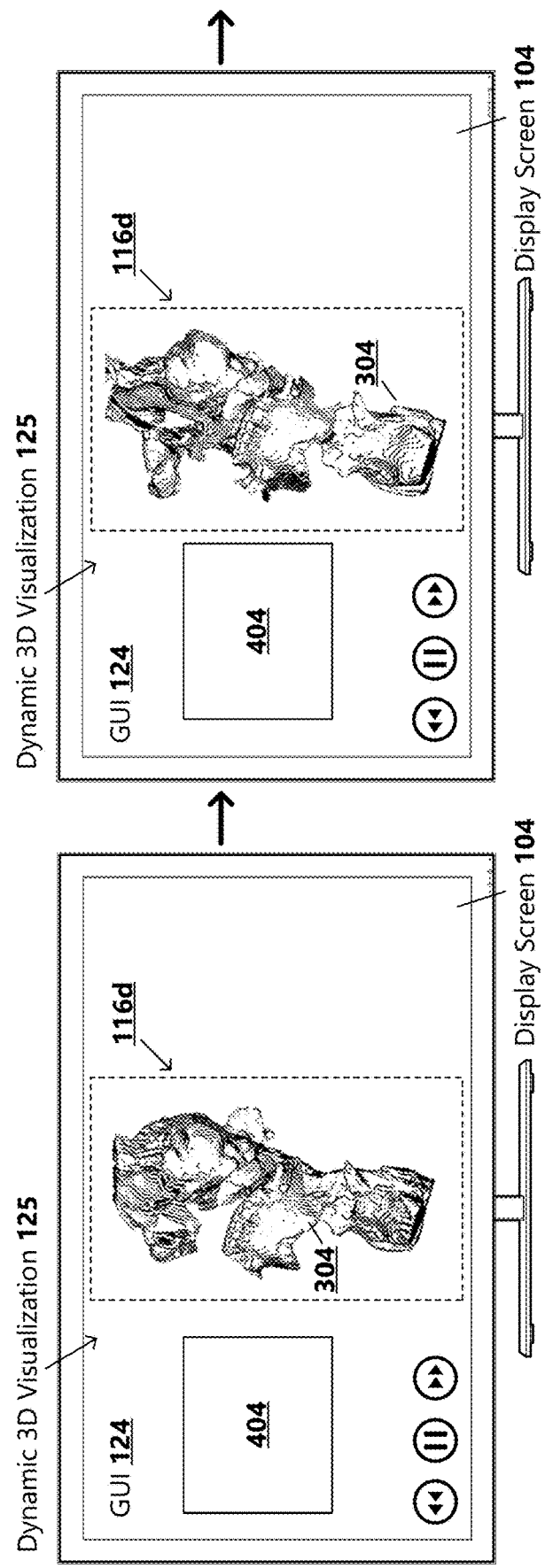

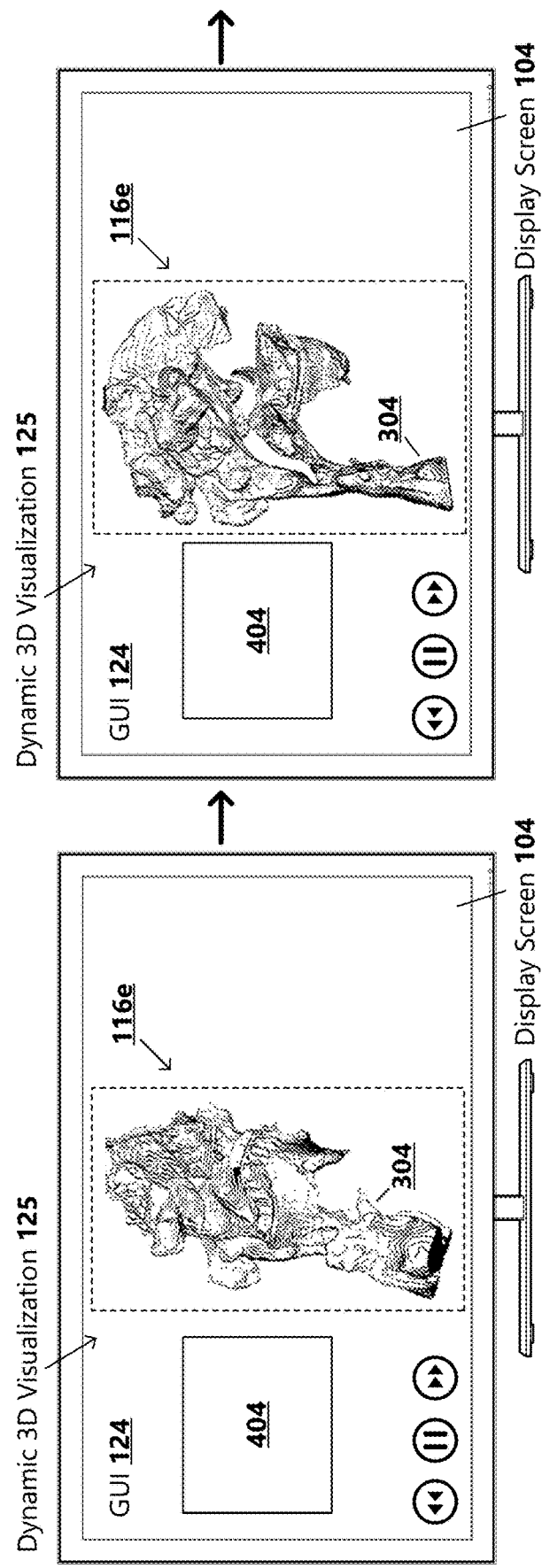

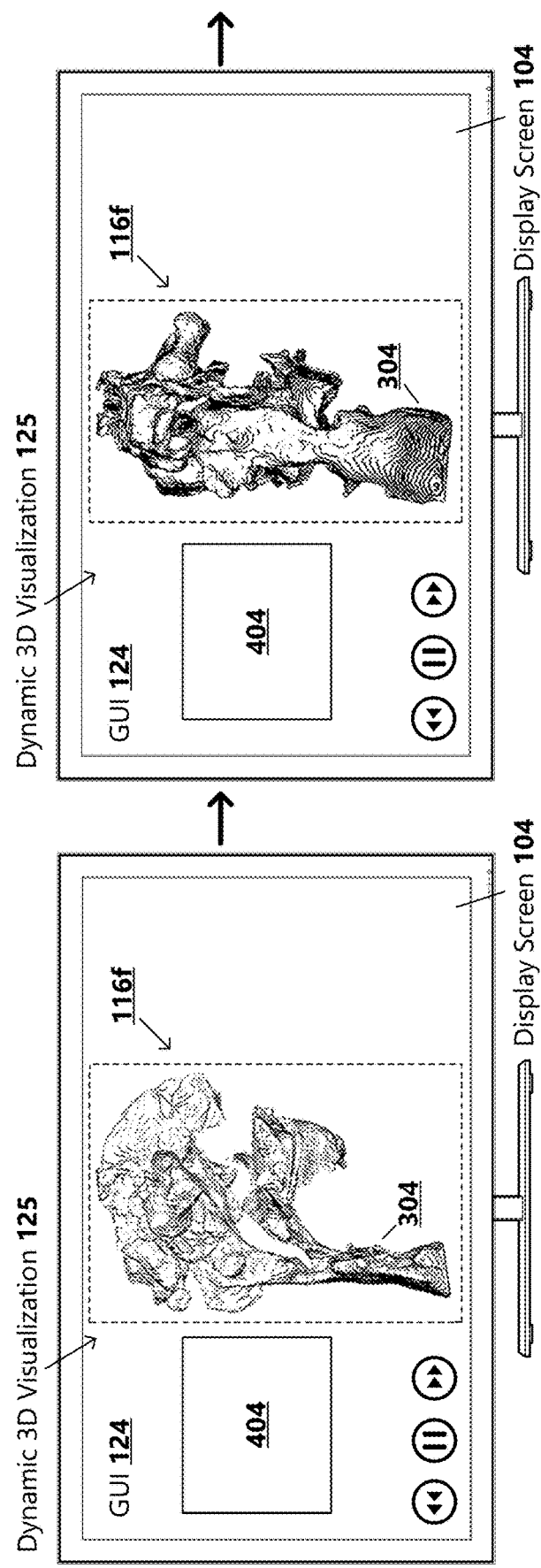

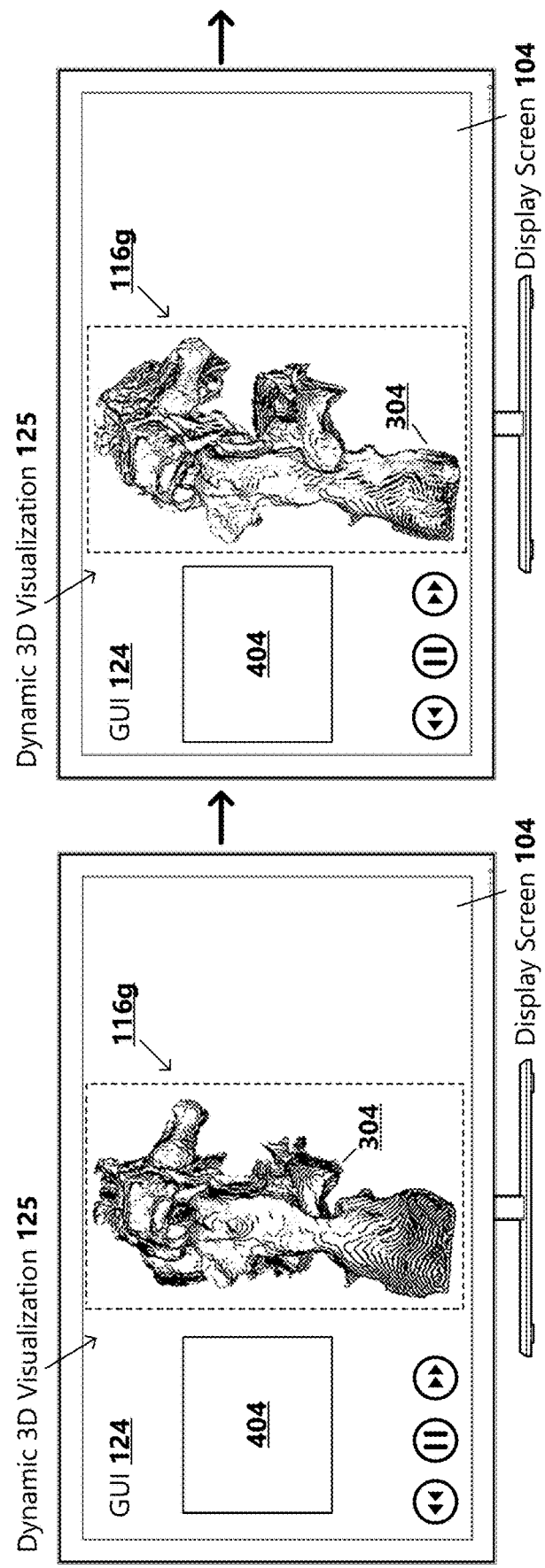

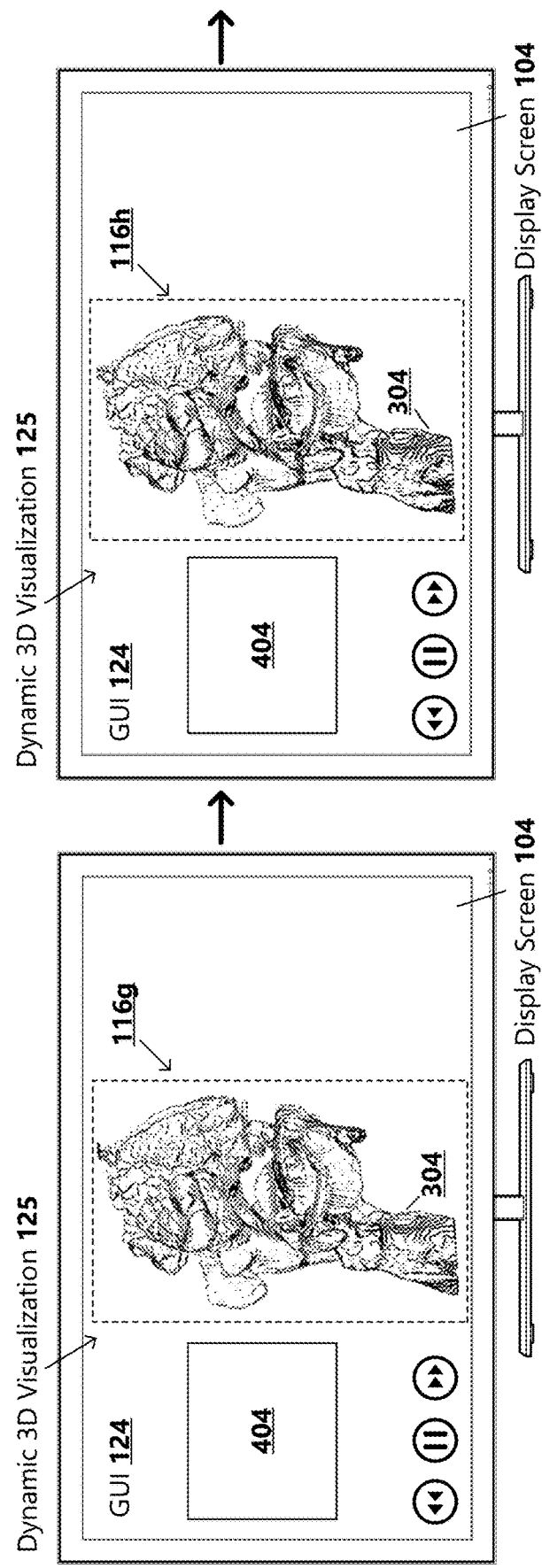

DYNAMIC 3-D ANATOMICAL MAPPING AND VISUALIZATION

CROSS REFERENCE TO RELATED APPLICATIONS

This application claims the benefit of U.S. Provisional Application No. 62/955,657, having the title of "Dynamic 3-D Anatomical Mapping and Visualization" and the filing date of Dec. 31, 2019, which is incorporated herein by reference in its entirety.

BACKGROUND

Various health problems can be associated with the obstruction of and/or the constriction of certain body cavities. As an example, the collapsibility of an airway can have a correlation to the severity of certain health conditions such as sleep apnea or hypoxia, or consequences of co-morbidities in patients. Accordingly, evaluation of a body cavity, such as a person's airway, can enable an identification of the person's anatomic risk factors, for determining a therapy for treating or managing an identified problem, and/or for determining the efficacy of a treatment. Current methods of diagnostic and therapeutic investigation of human body cavities may employ various technologies, such as computed tomography, X-rays, Lateral Cephalometrics, ultrasound, acoustic reflection technology, etc. However, current technologies for providing visualization of an airway are limited to 2-dimensional (2D) visualizations or static 3-dimensional (3D) visualizations.

For example, acoustic reflection technology utilizes an acoustic reflection measurement device, such as a Pharyngometer® or Rhinometer, to project sound waves down a person's airway, which are reflected back out in such a way that the relationship between the cross-sectional area of the airway and distance down the airway can be analyzed, quantified, and graphically displayed on a 2D line graph. An operator (user) may use the acoustic reflection measurement device to collect data at various points of a patient's inspiration or expiration. These static captures of data may be displayed as a plurality of 2D line graphs, and changes in the patient's airway may be identified by observing changes amongst the plurality of 2D line graphs.

An example of an imaging technique oftentimes used by medical professionals to generate a 3D image of an anatomical area of interest of a patient is cone beam computed tomography (CBCT). A CBCT system uses a CBCT scanner that rotates around the patient, capturing data using a cone-shaped X-ray beam. These data are used to reconstruct a 3D image of the patient's anatomy (e.g., dental (teeth); oral and maxillofacial region (mouth, jaw, and neck); or ears, nose, and throat). The 3D anatomical data produced by a CBCT system can be manipulated and analyzed for more precise diagnosis, evaluation, and treatment planning than conventional dental or facial X-rays. As can be appreciated and as will be discussed in further detail herein, a CBCT image is a static capture of anatomical area of interest at a moment in time.

Accordingly, a method and system are needed for improved anatomical imaging for improved anatomical visualization, communication, research, and metrics. It is with respect to these and other general considerations that embodiments have been described. While relatively specific problems have been discussed, it should be understood that the embodiments should not be limited to solving the specific problems identified in the background.

SUMMARY

The disclosure generally relates to a system and method for providing dynamic 3D anatomical visualization. Aspects of a 3D Rendering and Enhancement of Acoustic Data (READ) system described herein generate a 3D visual representation of an anatomic region of interest that may be dynamically transformed to characterize the movements of and/or changes to the region of interest. For example, the 3D visual representation may be a computer aided design (CAD) model that is generated based on an integration of static 3D image data, such as a set of cone beam computerized tomography (CBCT) images, and acoustic reflection measurements, such as the cross-sectional areas (CSA), length, and volume measurements of the airway determined and provided by an acoustic reflection measurement device (e.g., a Pharyngometer® (ECCOVISION of North Miami Beach, Fla.) and Rhinometer). The movements and/or changes to the region of interest may be determined based on real-time dynamic readings taken by the acoustic reflection measurement device, and the 3D visual representation may be transformed in real-time based on the dynamic readings. The transformation of the 3D visual representation may provide an animated visualization of the airway as the patient breathes, when the patient performs a Mueller's manoeuvre, and/or in response to mandibular repositioning, such as when fitting the patient for an oral appliance. The dynamic 3D visual representation provides a more anatomically-correct representation of the patient's anatomy (e.g., in comparison with a 2D representation), and can enable a user (e.g., healthcare professional/provider, patient) to visually assess changes in the oral and pharyngeal regions of the patient in real-time. The dynamic 3D visual representation may provide the healthcare provider with information on specific sites of airway obstruction, such as discrimination and degree of compliance of location(s) of obstruction, before and after treatment, with or without an oral appliance, etc., which provides improvements to the analysis and comprehension of the anatomy of the patient.

In a first aspect, a system for providing dynamic 3D visualization of an anatomical region of interest of an individual is provided. In an example embodiment, the system includes at least one processor, a memory storage device including instructions that when executed by the at least one processor are configured to receive static 3D image data representing the anatomic region of interest, wherein the anatomic region of interest comprises one or more anatomic landmarks, and acoustic measurement data representing the anatomic region of interest including the one or more anatomic landmarks, wherein the acoustic measurement data comprises continual acoustic measurements of the anatomic region; map the acoustic measurement data to the static 3D image data based on the one or more anatomic landmarks; generate a dynamic 3D visualization of the anatomic region by transforming the 3D visualization based on the acoustic measurements of the one or more anatomic landmarks; and provide the 3D dynamic visualization on a display screen.

In another aspect, a method for providing dynamic 3D visualization of an anatomical region of interest of an individual is provided. In an example embodiment, the method comprises receiving static 3D image data representing the anatomic region of interest, wherein the anatomic region of interest comprises one or more anatomic landmarks; receiving acoustic measurement data representing the anatomic region of interest including the one or more anatomic landmarks, wherein the acoustic measurement data comprises continual acoustic measurements of the anatomic region; mapping the acoustic measurement data to the static 3D image data based on the one or more anatomic landmarks; generating a dynamic 3D visualization of the anatomic region by transforming the 3D visualization based on the acoustic measurements of the one or more anatomic landmarks; and providing the 3D dynamic visualization on a display screen.

In another aspect, a computer readable storage media for providing dynamic 3D visualization of an anatomical region of interest of an individual is provided. In an example embodiment, the computer readable storage media comprises includes executable instructions which, when executed by a processor provide dynamic 3D visualization of an anatomic region of interest of an individual, the instructions comprising: receiving static 3D image data representing the anatomic region of interest, wherein the anatomic region of interest comprises one or more anatomic landmarks; receiving acoustic measurement data representing the anatomic region of interest including the one or more anatomic landmarks, wherein the acoustic measurement data comprises continual acoustic measurements of the anatomic region; mapping the acoustic measurement data to the static 3D image data based on the one or more anatomic landmarks; generating a dynamic 3D visualization of the anatomic region by transforming the 3D visualization based on the acoustic measurements of the one or more anatomic landmarks; and providing the 3D dynamic visualization on a display screen.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

Non-limiting and non-exhaustive examples are described with reference to the following figures.

DETAILED DESCRIPTION

Figure 1:
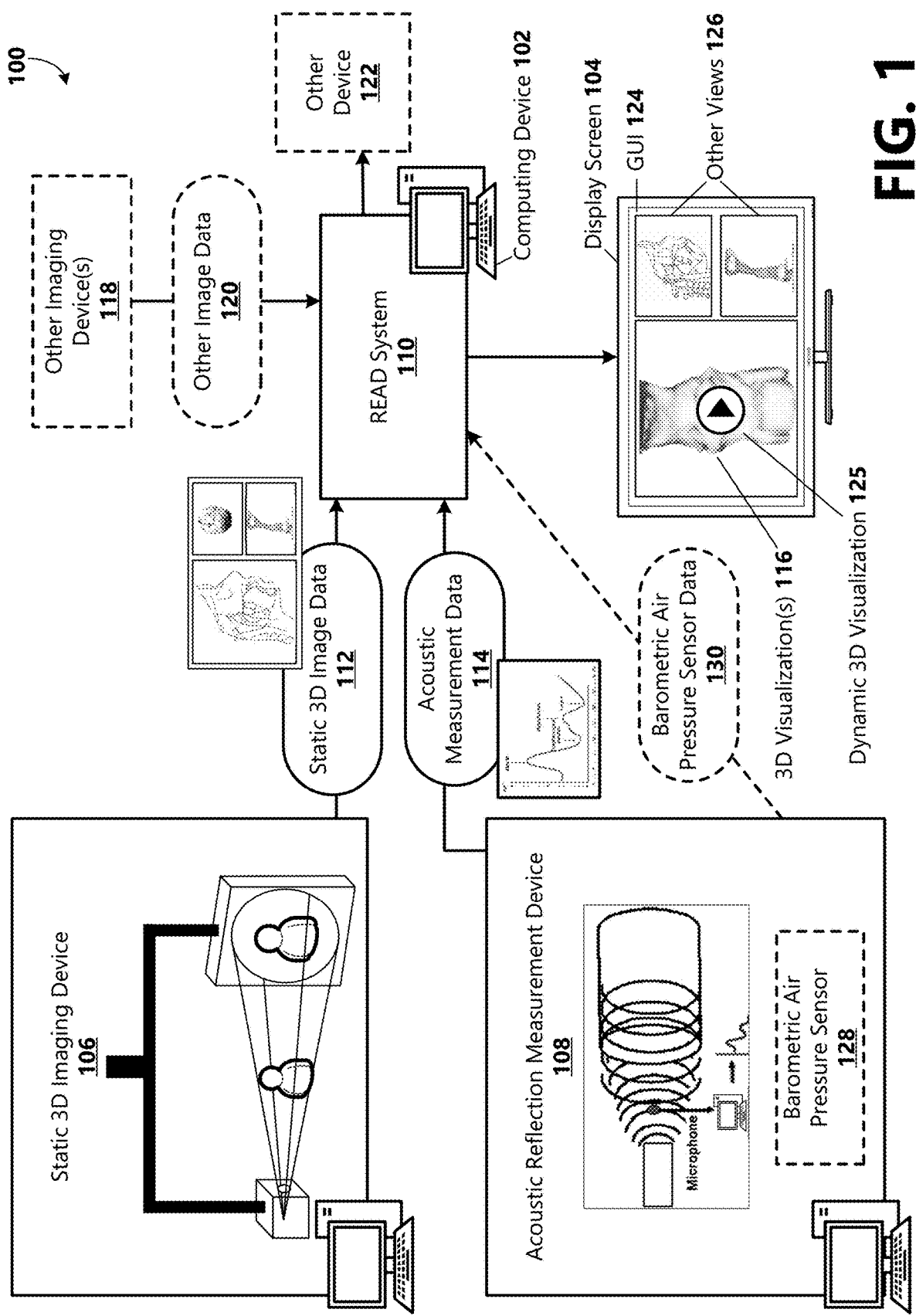
FIG. 1 is a block diagram of an example environment in which a system of the present disclosure can be implemented.

The following detailed description refers to the accompanying drawings. Wherever possible, the same reference numbers are used in the drawings and the following description to refer to the same or similar elements. While aspects of the present disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the present disclosure, but instead, the proper scope of the present disclosure is defined by the appended claims. Examples may take the form of a hardware implementation, or an entirely software implementation, or an implementation combining software and hardware aspects. The following detailed description is, therefore, not to be taken in a limiting sense.

The present disclosure provides systems and methods for optimizing anatomic visualization of a patient by generating a 3D visual representation of an anatomic region of interest that may be dynamically transformed to characterize the movements of and/or changes to the region of interest. FIG. 1 is a block diagram of an example environment 100 in which a 3D Rendering and Enhancement of Acoustic Data (READ) system 110 of the present disclosure can be implemented. As illustrated, the example environment 100 includes one or more computing devices 102. The READ system 110, sometimes hereinafter referred to as system 110, is illustrative of a computing device 102 or module, or a software application that can be executed by a computing device 102, which includes sufficient computer executable instructions, which when executed, are operative or configured to perform functionalities as described herein for providing dynamic 3D visual representations of anatomic regions of interest. Applications may include thick client applications, which may be stored locally on the computing device 102, or may include thin client applications (i.e., web applications) that may reside on a remote server and be accessible over a network or combination of networks (e.g., the Internet, wide area networks, local area networks). The computing device 102 may comprise or may be communicatively attached to a display screen 104. In some examples, the display screen 104 may include 3D goggles. According to examples, a graphical user interface (GUI) 124 may be provided and may be displayed on the display screen 104 for displaying dental images (including a dynamic 3D visualization 125 comprised of a plurality of 3D visualizations 116) and for enabling a user (e.g., healthcare provider) to interact with functionalities of the READ system 110 through manipulation of graphical icons, visual indicators, and the like. In some examples, the GUI 124 may be configured to utilize natural interface technologies that enables a user to interact with data and visualizations provided by the READ system 110 in a "natural" manner (e.g., methods that may rely on speech recognition, touch and stylus recognition, gesture recognition both on screen and adjacent to the screen, air gestures, head and eye tracking, voice and speech, vision, touch, hover, gestures). An example functionality of the READ system 110 includes tools that enable the user to view and manipulate the dynamic 3D visualization 125, the 3D visualizations 116, and/or image data used to generate the 3D visualizations and the dynamic 3D visualization.

The computing device 102 may be one or more of various types of computing devices (e.g., a server device, a desktop computer, a tablet computing device, a mobile device, a laptop computer, a laptop/tablet hybrid computing device, a large screen multi-touch display, or other type of computing device) configured to execute instructions for performing a variety of tasks. The hardware of these computing devices is discussed in greater detail in regard to FIG. 5.

The READ system 110 is operative or configured to receive multimodal image data from a plurality of image data sources, and to generate a plurality of 3D visualizations 116 and a dynamic 3D visualization 125 based on the received data for display on the display screen 104. According to an aspect, a first set of image data received by the READ system 110 may include static 3D image data 112 representing upper airway anatomy image information obtained from a static 3D imaging device 106 (e.g., CBCT device, magnetic resonance imaging (MRI) device, ultrasound). For example, the static 3D imaging device 106 may be configured to rotate over the anatomic region of interest of a patient, and acquire a set of 2D images or image slices that can be digitally combined to form a 3D image or volumetric data set. The static 3D image data 112 may include visualizations (e.g., sagittal, axial, coronal, and 3D views), measurements (e.g., volume and area measurements), and visual graphs of the patient's upper airway anatomy.

Currently, without implementation of aspects of the present disclosure, static 3D imaging, such as provided by a CBCT imaging device, although sufficient for identifying certain anatomical risk factors, such as establishing if there is a risk for airway instability, does not provide insight to a dynamic airway, and thus has limited usefulness. That is, a CBCT image (i.e., static 3D image data 112) is a static capture of a region of interest at a moment in time, which does not provide a way to visualize airway movement, size, or shape of dynamic anatomy, such as the human airway at various positions, while wearing an oral appliance, or during activities such as inhaling, exhaling, gasping, choking, swallowing, etc. For example, to visualize a patient's airway response to repositioning using CBCT, multiple images may need to be taken which increases the patient's exposure to radiation. Additionally, using CBCT to determine oropharyngeal instability currently involves evaluating the Anterior-Posterior (A-P) cross sectional diameter and/or air volume at the most compliant point of an airway of the patient with the patient's teeth positioned together, which does not provide data for enabling a healthcare professional to assess changes in airway stability with changes in vertical displacement of the mandible. Accordingly, utilization of CBCT without aspects of the present disclosure does not allow the healthcare provider to visualize or measure the changes to a patient's airway when repositioning the mandible in various dimensions, such as when testing potential responsiveness to oral appliance therapy.

The static 3D image data 112 may be formatted based on a standard format protocol, such as DICOM® (Digital Imaging and Communications in Medicine) or other standard format that enables digital medical imaging information and other related digital data to be transmitted, stored, retrieved, printed, processed, and displayed. The static 3D imaging device 106 may or may not be located at the location or site of the READ system 110. For example, the static 3D image data 112 may be generated by the static 3D imaging device 106 at a location remote from the READ system 110, and may be received by the READ system over a network or other communications medium. In some examples, the static 3D image data 112 may be stored on a data storage device and read by the READ system 110.

According to an aspect, a second set of image data received by the READ system 110 may include a first set of acoustic measurement data 114 representing upper airway anatomy image information obtained from one or more acoustic reflection measurement devices 108 (e.g., a Pharyngometer® and Rhinometer, other acoustic measurement device). The static 3D image data 112 (first set of image data) and the first set of acoustic measurement data 114 at least in part represent common upper airway anatomy of the patient. The acoustic reflection measurement device 108 may be configured to use a reflection of acoustic waveforms to calculate the cross-sectional areas (CSA), length, and volume of the upper airway of the same patient. These acoustic measurement data 114 may be represented as 2D line graphs depicting the cross-sectional area of the airway as a function of distance. To obtain measurements of at least the nasal cavity and nasopharynx portion of the patient's airway, the acoustic reflection measurement device 108 may emit a pulsing sound into the patient's nasal cavity through a wave tube as the patient exhales through the wave tube. To obtain measurements of at least the pharyngeal portion of the patient's airway, the acoustic reflection measurement device 108 may emit a pulsing sound into the patient's upper airway through the wave tube as the patient exhales through a mouthpiece attached to the wave tube. The acoustic reflection measurement device 108 may be configured to use the reflected acoustic waves to calculate the cross-sectional area of the airway as a function of distance down the airway. According to an aspect, the acoustic reflection measurements may be taken while the patient is in a same position (e.g., supine, seated upright in a chair with a neutral head position) as when the static 3D image data 112 were obtained. According to another aspect, the first set of acoustic measurement data 114 and the static 3D image data 112 may be acquired while the patient is performing a same respiration procedure, such as a Müller's maneuver or a modified Müller's maneuver where the airway may be collapsed after a forced expiration and an attempt at inspiration is made with a closed mouth and nose (or closed glottis).

In some examples, the acoustic measurement device 108 may include a barometric air pressure sensor 128 which may be used to record and provide barometric air pressure sensor data 130 to the READ system 110. In some examples, an indication (e.g., audible, visual, tactile) of the barometric air pressure sensor data 130 may be provided, such as an alert that may be provided when a particular air pressure reading is sensed (e.g., when the air pressure reading reaches a threshold value, when the air pressure reading is equal to the ambient air pressure). The barometric air pressure sensor 128 may be located in a mouthpiece portion of the acoustic measurement device 108. In some examples, the barometric air pressure sensor data 130 may be utilized to determine when air has been fully expelled from the patient's upper airway while performing a Müller's maneuver or a modified Müller's maneuver. For example, the barometric air pressure sensor data 130 may provide an indication to a user (e.g., healthcare provider/clinician) that a certain threshold has been reached and that acoustic reflection measurements obtained while the threshold is reached may be analyzed for determining an airway collapse event and a degree of the airway collapse. For example, while performing a modified Müller's maneuver, a first patient may only expel a fraction of their total air volume where a second patient may perform a full expulsion. The barometric air pressure sensor data 130 may be used as an indication that the first patient may need to expel more air for obtaining acoustic measurements associated with an airway collapse event. In some examples, the barometric air pressure sensor data 130 may be utilized to reduce variability in acoustic measurements and for enabling a more similar comparison between acoustic measurement datasets and visualizations.

In some examples, the patient may use a head positioning device and/or a mandibular positioning device during the capture of the static 3D image data 112 and during the capture of the first set of acoustic measurement data 114 to ensure similar positioning for more accurate registration of anatomic landmarks between the image data sets. For example, the first set of acoustic measurement data 114 may be used as a baseline recording.

To obtain measurements that enable a determination of an airway collapse event, the discrimination or degree of compliance of location(s) of obstruction, during different phases of breathing, before and after treatment, with or without an oral appliance, etc., one or more additional acoustic reflection measurements may be obtained, and additional sets of acoustic measurement data 114 comprising a plurality of acoustic measurements may be transmitted to the READ system 110. In some examples, the additional acoustic reflection measurements may be obtained while the patient is breathing to capture changes to the patient's airway while breathing. In some examples, the additional acoustic reflection measurements may be obtained while the patient is performing a modified Müller's maneuver. In further examples, the additional acoustic reflection measurements may be obtained during repositioning of the patient's mandible in various mandibular translations and rotations (e.g., vertical, AP (anteroposterior) and lateral, plus one or more of the angles of rotation about the axes of these dimensions: pitch, roll and yaw). It is to be appreciated that "roll," "pitch" and "yaw" constitute rotational descriptors. If the AP, lateral and vertical dimensions of occlusion are seen as axes, roll, pitch and yaw may be seen as rotation about the axes, with yaw constituting rotation about the vertical axis, pitch constituting rotation about the lateral axis and roll constituting rotation about the AP axis. In some examples, the one or more additional acoustic reflection measurements may be obtained during a fitting process of an oral appliance. In some examples, a therapeutic position verifying tool, such as the therapeutic position verifying tool described in the patent application of Jerry C. Hu, Ser. No. 16/573,932 filed Sep. 17, 2019, may be used during the fitting process to set vertical, anterior-posterior, and lateral occlusion dimensions to be set and measured with the acoustic reflection measurement device 108. Other example positioning tools may include airway metrics jigs, a George Gauge™, an Andra™ Gauge, an apnea guard, etc.

In some examples, the acoustic reflection measurement device 108 is configured to continually obtain additional acoustic reflection measurements for a time duration and to provide acoustic measurement data 114 corresponding to the additional acoustic reflection measurements to the READ system 110 in a continual stream or as a batch. Currently, without implementation of aspects of the present disclosure, an operator (user) may use the acoustic reflection measurement device 108 to collect data at various points of a patient's inspiration or expiration. These static captures of data may be displayed as a plurality of 2D line graphs, and changes in the patient's airway may be identified by observing changes amongst the plurality of 2D line graphs. While the resulting data points and metrics can provide useful information when assessing a person at risk for certain disorders, such as obstructive sleep apnea (OSA), actual dynamic movements and changes of the patient's airway are not provided by current acoustic reflection measurement device technologies. For example, a video playback feature, such as what is provided by aspects of the present disclosure, may enable new studies of patients' airways where new metrics may be observed.

As will be described in further detail below, aspects of the READ system 110 are configured to provide a real-time display of changes to the patient's airway in 3D based on a received stream of acoustic measurement data 114. As used herein, the term "real-time," such as used to describe the dynamic display of changes to the patient's airway, may include minor processing or data transmission lag and may therefore describe "near real-time" displays of changes to the patient's airway. That is, the term "real-time" is used herein to describe an ability of the READ system 110 to generate and display a dynamic 3D visualization 125 corresponding to measurements of the patient's airway as the measurements are obtained, rather than a later composition of images on a separate system to provide an after-the-fact 3D display. In some examples, the READ system 110 is further configured to generate 3D visualizations 116 based on previously-obtained measurements and to provide an after-the-fact dynamic display of the 3D visualizations 116. The additional acoustic reflection measurements provided by the acoustic reflection measurement device 108 may be obtained based on a preset time interval (e.g., automatically) and/or responsive to a manual selection/actuation initiated by a user/healthcare provider. According to some aspects, the acoustic reflection measurement device 108 may be located at a same location or site as the READ system 110. According to other aspects, the acoustic measurement data 114 may be obtained at a location remote from the READ system 110, and may be transmitted to and received by the READ system over a network or other communications medium.

In some examples, one or more sets of other image data 120 may be obtained by one or more other imaging devices 118 and provided to the READ system 110. For example, the one or more sets of other image data 120 may comprise 2D and/or 3D digital photograph data of the patient's face and/or head produced by a digital camera, intraoral scan data generated by an intraoral scanner, X-Ray scan data, MRI scan data, CT scan data, ultrasound scan data, or other dental imaging data provided by other dental imaging devices 118.

As will be described in further detail below, the READ system 110 is configured to receive the image data (i.e., static 3D image data 112, the acoustic measurement data 114, and optionally the other image data 120), to register the received image data based on one or more anatomic landmarks, and to generate a morph-able 3D model or representation of at least the patient's airway. In some examples, the other image data 120 may include a photographic image or other scan image of the patient that may be superimposed on the 3D representation of the patient's airway and used to generate a layered 3D visualization 116 of the patient. Based on the one or more additional sets of acoustic measurement data 114 obtained from the acoustic reflection measurement device 108, the 3D visual representation 116 may be dynamically transformed in real-time. That is, a dynamic 3D visualization 125 is generated that may be configured to dynamically morph or transform to correspond to movements and/or changes (e.g., shape, size, obstructions) to the region of interest as determined based on the one or more additional sets of acoustic measurement data 114. Accordingly, a dynamic 3D visualization 125 of the airway may be generated and displayed as the patient breathes, when patient performs a Mueller's manoeuvre, in response to mandibular repositioning, such as when fitting the patient for an oral appliance, etc.

According to an aspect, the dynamic 3D visualization 125 may include a video playback of a representation of the acoustic measurement data 114 so that actual dynamic movements and changes can be played back as a video and rendered on the display screen 104 in the GUI 124 provided by the READ system 110. The GUI 124 may configured to simultaneously display one or more other views 126 (e.g., axial, sagittal, coronal) of the anatomic region of interest. The other views 126 may include one or more images included in the static 3D image data 112, one or more representations of the acoustic measurement data 114, one or more images of the other image data 120, and/or combinations of one or more of the above. In some examples, the READ system 110 may be further configured to register other images of the anatomic region of interest with the acoustic measurement data 114 based on one or more anatomic landmarks, and to generate one or more additional morph-able 2D or 3D representations of at least the patient's airway. Based on the one or more additional sets of acoustic measurement data 114 obtained from the acoustic reflection measurement device 108, the additional 2D or 3D representation(s) may also be dynamically transformed in real-time. According to an aspects, the READ system 110 may be further configured to capture a recording of the dynamic 3D visualization 125. For example, the READ system 110 may store the recording of dynamic movements of and/or changes to the patient's airway for later playback and display on a display screen 104.

In some examples, the environment 100 may further include one or more other devices 122 that may be operative or configured to receive dynamic 3D visualization data from the READ system 110. For example, the READ system 110 may generate and provide data associated with the 3D visualizations 116 and/or the dynamic 3D visualization 125 in a format that can be transmitted to and used by a 3D printer to print a 3D model of the 3D visualization, virtual reality or augmented reality glasses to generate a display of the dynamic 3D visualization 125, or another type of other device 122 to generate another type of representation of the 3D visualizations 116 and/or the dynamic 3D visualization 125 or for other diagnostic or therapeutic use. In some examples, data associated with the 3D visualizations 116 and/or the dynamic 3D visualization 125 may include measurements, positioning data, and/or other data that can be used for generating a custom oral appliance prescription, a growth guidance appliance, or other use.

Figure 2:
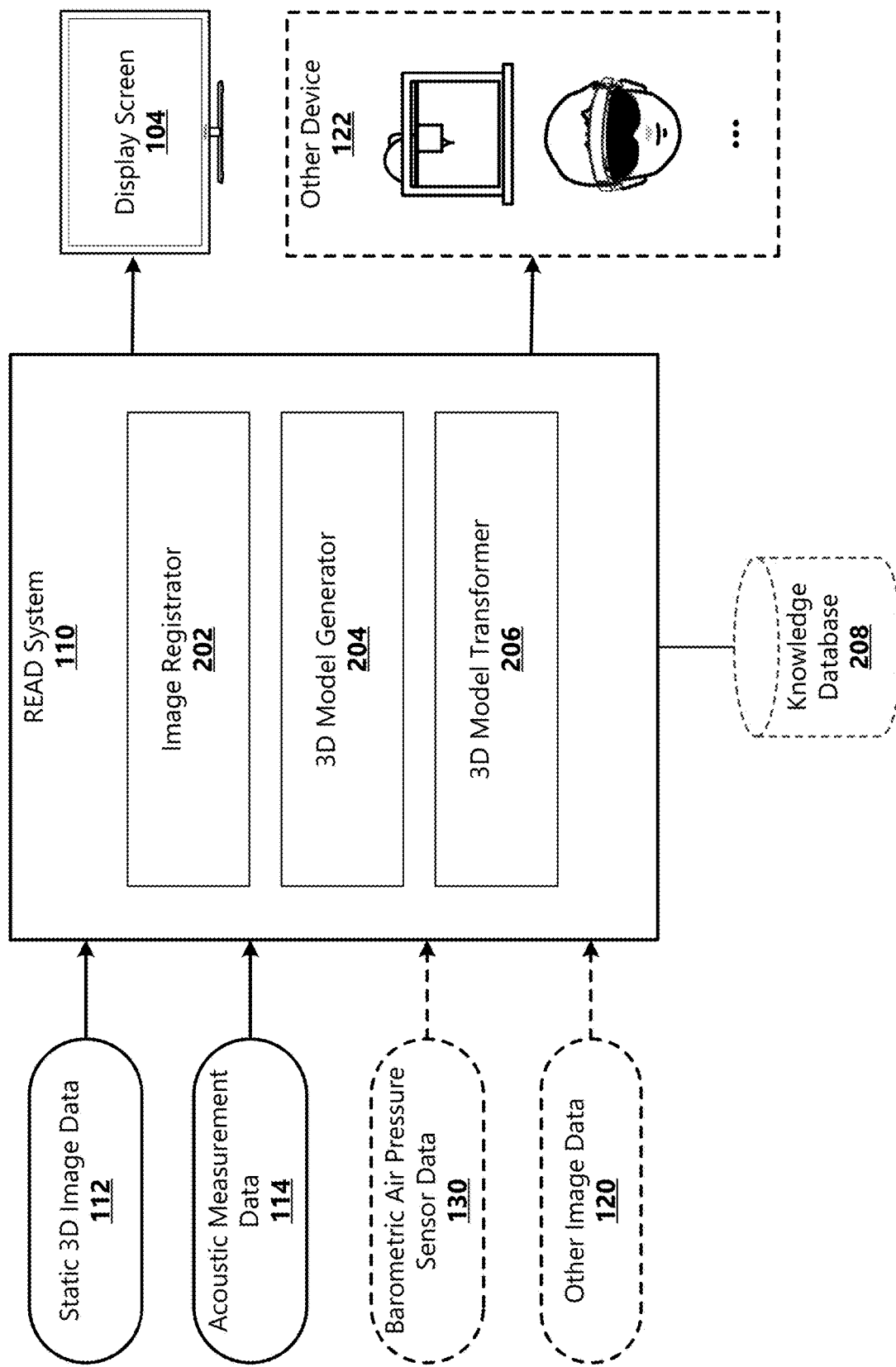
FIG. 2 is a block diagram showing components of an example system of the present disclosure.

FIG. 2 is a block diagram showing various components of an example READ system 110. With reference now to FIG. 2, the example READ system 110 may include an image data registrator 202, a 3D model generator 204, and a 3D model transformer 206. As should be understood by those skilled in the art, one or more of the components (e.g., image data registrator 202, a 3D model generator 204, and a 3D model transformer 206) can be integrated or provided in any combination of separate systems, wherein FIG. 2 shows only one example.

Figure 3:
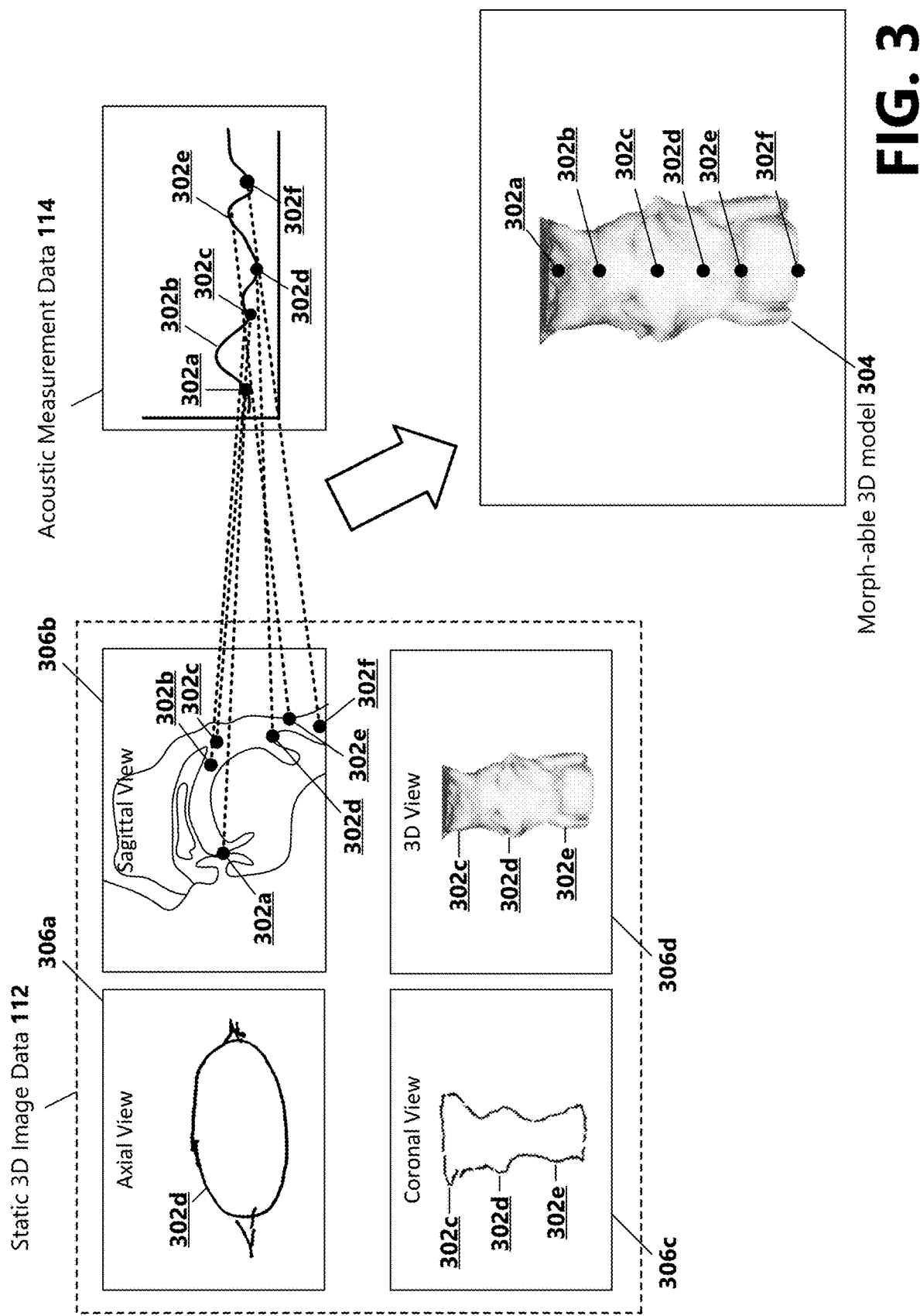
FIG. 3 illustrates example anatomic landmarks of at least a portion of a patient's airway registered between multimodal image data.

The image data registrator 202 is illustrative of a software application, module, or computing device, operative or configured to register the first set of acoustic measurement data 114 to the static 3D image data 112. For example, as part of registering the first set of acoustic measurement data 114 to the static 3D image data 112, the image data registrator 202 is operative or configured to map one or more anatomic landmarks associated with an automatically-selected or manually-selected anatomic region of interest defined in the first set of acoustic measurement data 114 to one or more corresponding anatomic landmarks identified in the static 3D image data 112. In some aspects and as illustrated in FIG. 3, multi-planar visualization of the static 3D image data 112 may be used to identify the one or more particular anatomic landmarks 302*a-n* (generally 302) of at least a portion of a patient's airway (e.g., nasal cavity, nasopharynx portion, and/or pharyngeal portion) in the static 3D image data 112. For example, one or more of the various views 306*a-d* (sagittal, coronal, axial, 3D views) of the anatomic region of interest included in the static 3D image data 112 may reveal the one or more particular anatomic landmarks 302 (e.g., the oral cavity, nasal cavity, oropharyngeal junction (OPJ), oropharynx, epiglottis, hypopharynx, velopharynx, glottis, incisive papilla, hyoid bone, mental foramen, maxillary tuberosity), which may be identified via a manual process (e.g., one or more slices or views of the static 3D image data 112 may be displayed, and the user may visually identify the one or more particular anatomic landmarks 302 and define (e.g., digitally place markers on) the one or more identified landmarks), an automatic process (e.g., the image data registrator 202 may be configured to automatically detect one or more particular anatomic landmarks 302 in one or more slices or views of the static 3D image data 112), or a hybrid process (e.g., one or more particular anatomic landmarks 302 are automatically detected, and the user may manually adjust one or more of the landmarks with a GUI tool). In some examples, as part of identifying/defining an anatomic landmark 302 in the static 3D image data 112, the image data registrator 202 may be configured to determine measurements associated with the landmark (e.g., CSA measurements, distance measurements from one or more reference points) based on the one or more views 306*a-d* (sagittal, coronal, axial, 3D views) of the anatomic region of interest included in the static 3D image data 112. These anatomic landmark measurements may be used as part of mapping the landmark between the static 3D image data 112 and the acoustic measurement data 114.

The one or more particular anatomic landmarks 302 may also be identified/defined in the acoustic measurement data 114 via a manual, automatic, or hybrid process based on the airway measurements derived from the acoustic reflection measurement device 108. As an example, the oropharyngeal segment may be defined as the region between the proximal minimum and distal minimum cross-section areas, wherein these points correspond anatomically to the oropharyngeal junction and epiglottis and wherein these points can be identified from the acoustic reflection measurements. In some examples, as part of identifying an anatomic landmark 302 in the acoustic measurement data 114, the image data registrator 202 may be configured to determine measurements associated with the landmark (e.g., CSA measurements, distance measurements from one or more reference points). These anatomic landmark measurements may be used as part of mapping the anatomic landmark 302 between the static 3D image data 112 and the acoustic measurement data 114 and for identifying and tracking the anatomic landmark in additional acoustic measurement data 114 received by the READ system 110. In some examples, the READ system 110 includes a component (e.g., 3D model generator 204) operative or configured to generate a 3D representation of the anatomic region of interest based on the first set of acoustic measurement data 114 (e.g., the CSA measurements and distance measurements), and the one or more particular anatomic landmarks 302 may be identified in the 3D representation generated from the acoustic reflection measurements.

According to an aspect, after the one or more particular anatomic landmarks 302 are identified/defined in the received image data, the image data registrator 202 is further configured to map one or more of the particular anatomic landmarks 302 identified in the first set of acoustic measurement data 114 and the associated measurement data to the corresponding one or more anatomic landmarks 302 in one or more views 306 (e.g., sagittal, axial, coronal, and 3D views) included in the static 3D image data 112. In some examples, as part of mapping an anatomic landmark 302 between the first set of acoustic measurement data 114 and the static 3D image data 112, the READ system 110 is operative or configured to create a mapping between a corresponding anatomic landmark 302 based on a determined distance of the anatomic landmark 302 from one or more reference points. By mapping the one or more anatomic landmarks 302 between the first set of acoustic measurement data 114 and the static 3D image data 112, the READ system 110 is enabled to identify the anatomic landmark 302 and track changes in measurements (e.g., CSA measurements) of the landmark in additional acoustic measurement data 114 transmitted to the system 110 from the acoustic reflection measurement device 108.

In some examples, one or more sets of other image data 120 from one or more other imaging devices 118 may be received by the READ system 110 and registered to the static 3D image data 112 based on one or more anatomic landmarks 302. For example, the one or more sets of other image data 120 may be superimposed on the 3D representation of the patient's airway and used to generate a layered 3D visualization of the patient.

In some examples, barometric air pressure sensor data 130 provided by a barometric air pressure sensor 128 included in the acoustic reflection measurement device 108 may be received by the READ system 110 and used by the system to determine when the patient has performed a full expulsion of air (e.g., when a barometric air pressure reading indicates that a threshold air pressure value has been reached) and for determining whether acoustic measurement data 114 obtained during the full expulsion is indicative of an airway collapse event.

The 3D model generator 204 is illustrative of a software application, module, or computing device, operative or configured to generate a morph-able 3D model 304 representing at least the anatomic region of interest (e.g., at least a portion of the patient's airway) based on the static 3D image data 112 and the first set of acoustic measurement data 114. As should be appreciated, although the example 3D model 304 illustrated in FIG. 3 shows a portion (e.g., pharyngeal portion) of a patient's upper airway, other examples of the 3D model 304 may include additional portions (e.g., nasal cavity, nasopharynx portion). According to an aspect, the 3D model generator 204 may be configured to generate the morph-able 3D model 304 using CAD functionalities. One example embodiment of the 3D model generator 204 may be configured to access a 3D view or model of the patient's airway included in the static 3D image data 112 and convert the 3D view or model into the morph-able 3D model 304 that includes the identified/defined anatomic landmarks 302. Another example embodiment of the 3D model generator 204 may be configured to generate the morph-able 3D model 304 using CAD functionalities based on various views 306 (e.g., sagittal, axial, coronal) of the patient's airway included in the static 3D image data 112. According to an aspect, the 3D model generator 204 is configured to link the determined mappings between the one or more anatomic landmarks 302 in the first set of acoustic measurement data 114 and the static 3D image data 112 to the one or more anatomic landmarks 302 in the morph-able 3D model 304.

According to another embodiment, the 3D model generator 204 may be configured to generate a 3D representation of the anatomic region of interest based on the first set of acoustic measurement data 114 (e.g., the CSA measurements and distance measurements), and superimpose this 3D representation with a 3D view 306*d* of the anatomic region of interest included in the static 3D image data 112 based on the one or more identified/defined anatomic landmarks 302 to generate the morph-able 3D model 304.

According to an aspect, when the one or more additional sets of acoustic measurement data 114 are received from the acoustic reflection measurement device 108, the image registrator 202 may be further operative or configured to identify/define the one or more particular anatomic landmarks 302 in the additional acoustic measurement data 114 and to provide the associated location and measurements of the one or more anatomic landmarks 302 to the 3D model transformer 206.

The 3D model transformer 206 is illustrative of a software application, module, or computing device, operative or configured to receive one or more additional sets of acoustic measurement data 114 (e.g., location and measurements of the anatomic landmarks) and transform the morph-able 3D model 304 based on the additional acoustic measurement data 114 for providing a dynamic 3D visualization 125 of the patient's airway. According to an aspect, the 3D model transformer 206 may receive an additional set of acoustic measurement data 114 including updated measurements/positions of the one or more identified/defined anatomic landmarks 302, and based on the mappings to the landmarks in the various views 306 (e.g., sagittal, axial, coronal, 3D), the one or more landmarks may be transformed in the various views to represent the updated measurements/positions. Based on the transformations to the one or more anatomic landmarks 302 in the various views 306, the 3D model transformer 206 may update the morph-able 3D model 304. For example, the first 3D visualization 116 of the airway provided by the morph-able 3D model 304 may be transformed into a next 3D visualization 116 to match the determined measurements (or match a ratio of change of the determined measurements) of the airway based on the location and measurements of the anatomic landmarks 302. In an example, the dynamic 3D visualization 125 (comprised of the plurality of 3D visualizations 116) may provide a dynamic visualization of movement of the patient's anatomy, such as movements of various segments of the patient's airway, the patient's tongue, the hyoid bone, etc.

In some embodiments, the READ system 110 may further include a knowledge database 208 comprising a plurality of datasets of static 3D images (e.g., various views 306 of CBCT images) of airways of various patients. For example, the images included in the knowledge database 208 may be used by the 3D model transformer 206 as references to the geometries of the one or more anatomic landmarks 302 at various measurements. For example, an image included in the knowledge database 208 may include a particular anatomic landmark 302 that has the same or similar measurements as an updated measurement of the particular anatomic landmark 302 included in a received dataset of additional acoustic measurement data 114. Accordingly, the image included in the knowledge database 208 may be used by the 3D model transformer 206 as a target image for the updated measurement in a next 3D visualization 116.

In some example aspects, the 3D model transformer 206 may animate the transformation between the first 3D visualization 116 of the airway and the next to simulate actual movement, shape, and obstructions of the patient's anatomy. In some embodiments, colorization may be used by the 3D model transformer 206 to reflect changes in measurements of one or more anatomic landmarks 302 between visualizations 116.

In some examples, the READ system 110 may further include measurement tools configured to measure distances, diameters, etc., of anatomy represented in the static 3D image data 112, the acoustic measurement data 114, and/or in the generated 3D model 304. The READ system 110 may be further configured to convert the generated 3D visualizations 116 into various file formats for output to other systems or devices 122. For example, a visualization 116 may be converted into a universally accepted 3D file format, such as standard tessellation language (STL) or wavefront object (OBJ), which can be output to a 3D printer. As described above, the READ system 110 may include a component configured to capture a recording of the dynamic 3D visualization 125. For example, the READ system 110 may store the recording of dynamic movements of and/or changes to the patient's airway for later playback and display on a display screen 104 of the computing device 102 or of another device.

FIG. 3 illustrates example anatomic landmarks 302*a-f* (generally 302) registered between multimodal image data. As described above, particular anatomic landmarks 302 (e.g., the oral cavity, nasal cavity, oropharyngeal junction (OPJ), oropharynx, epiglottis, hypopharynx, velopharynx, incisive papilla, hyoid bone, mental foramen, maxillary tuberosity glottis, hyoid bone) in the static 3D image data 112 may be identified and mapped to the identified anatomic landmarks in the first set of acoustic measurement data 114. As can be appreciated, additional, fewer, or other anatomic landmarks 302 may be identified and mapped.

Figure 4A:
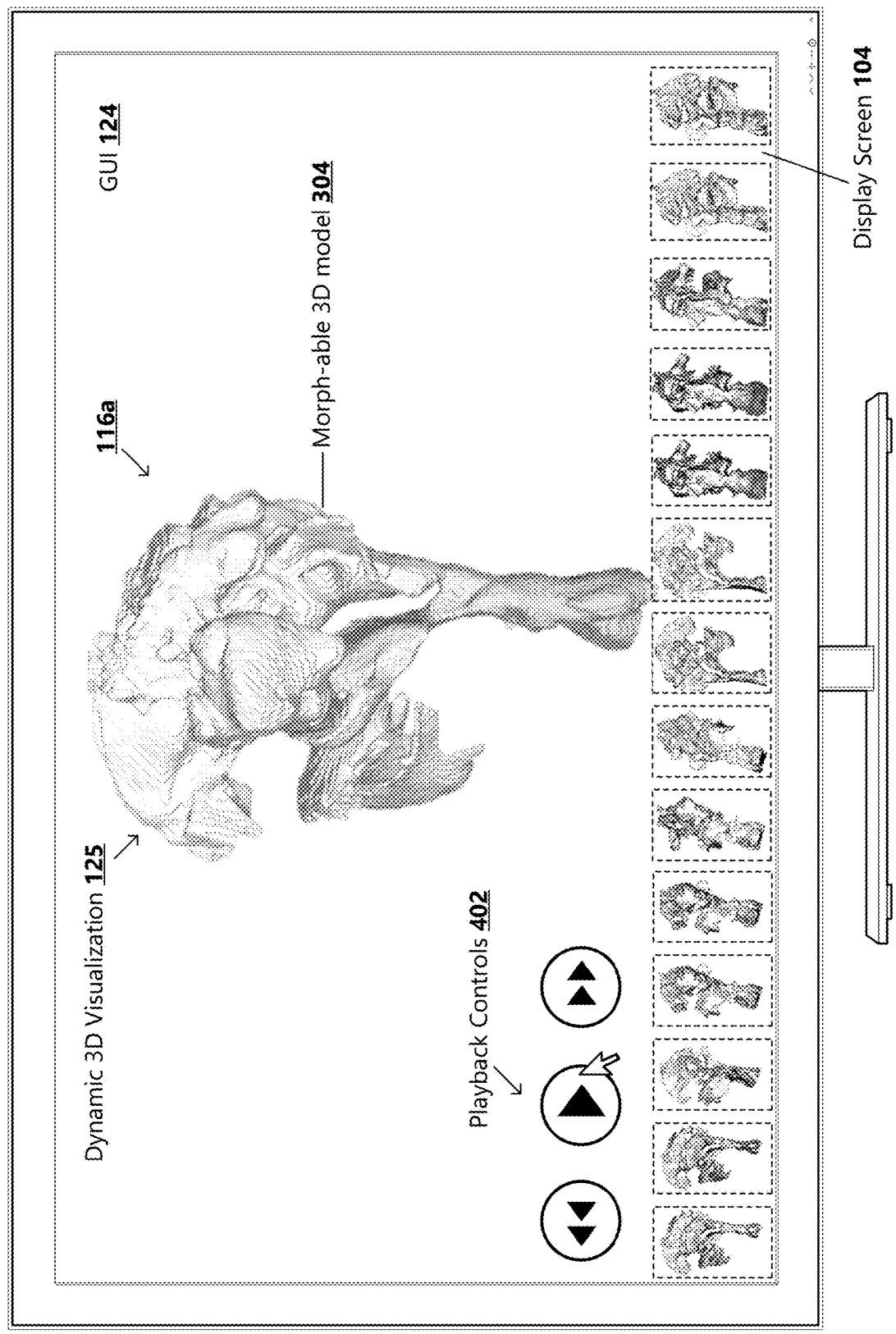
FIGS. 4A-O illustrate a display of a dynamic 3D visualization of the patient's upper airway generated by aspects of the present disclosure.
Figures 4D, 4E:
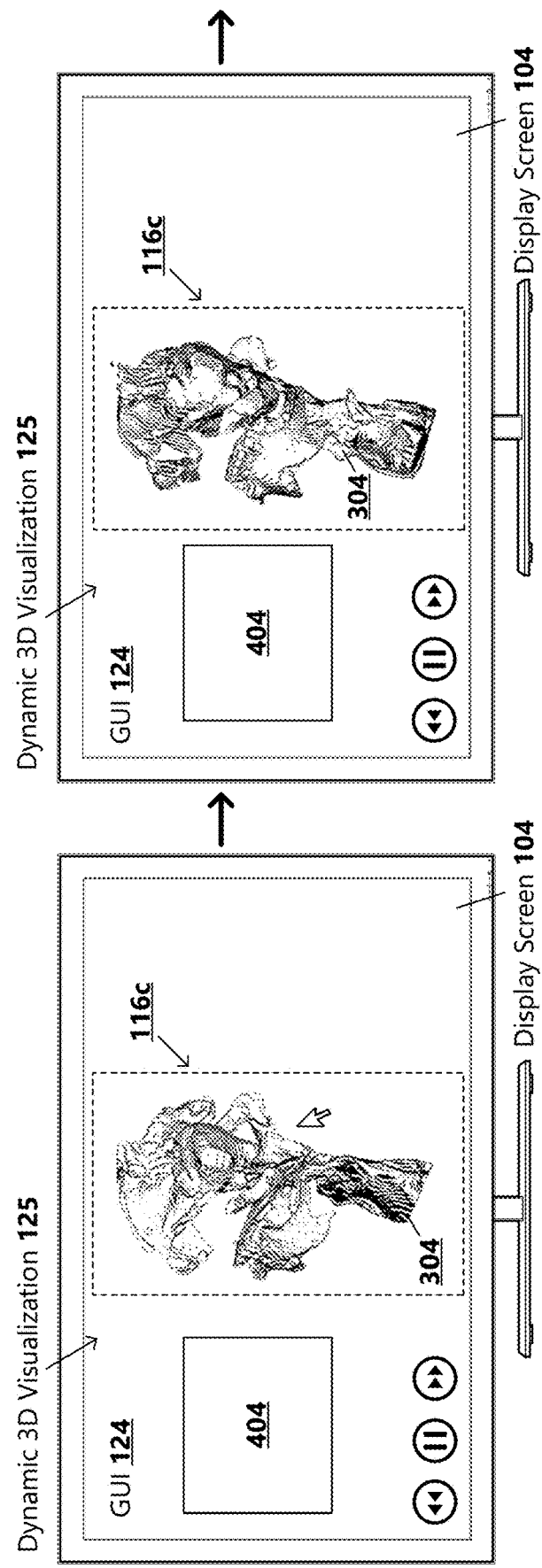
FIG. 4P illustrates an example 3D visualization of the patient's upper airway wherein colorization is utilized to represent measurement changes.
Figure 4P:
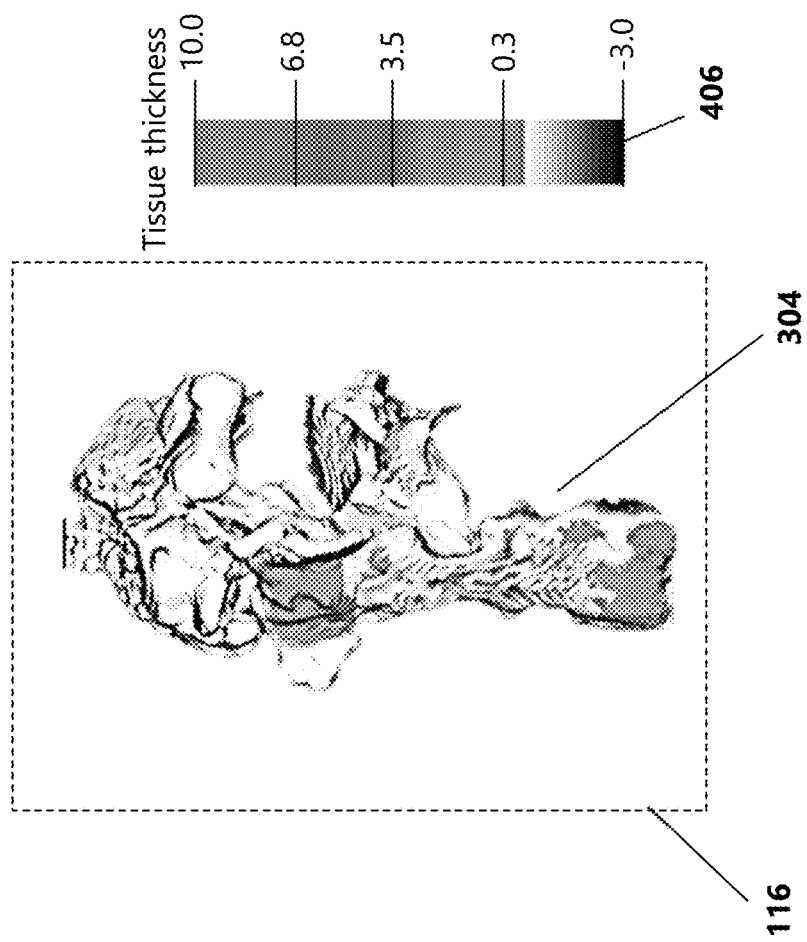

FIGS. 4A-4P illustrate example visualizations 116 of a morph-able 3D model 304, that when played, provide a dynamic 3D visualization 125 of the patient's airway. With reference now to FIG. 4A, an example first 3D visualization 116*a* of a plurality of 3D visualizations is shown displayed in an example GUI 124 displayed on an example display screen 104. In some examples, the display screen 104 may be embodied as 3D goggles. The example first 3D visualization 116*a* includes the morph-able 3D model 304 generated by aspects of the present disclosure as part of providing a dynamic 3D visualization 125 of the patient's airway. The dynamic 3D visualization 125 may be displayed in real-time based on received dynamic measurement readings. The first visualization 116*a* may represent the patient's airway (i.e., region of interest) while the patient is breathing in, breathing out, during a particular positioning of the mandible, while performing a Müller's maneuver, a modified Müller's maneuver, or other breathing process, etc. In some examples, playback controls 402 (e.g., a play button, a rewind button, a fast forward button, a pause button) may be provided in the GUI 124 for controlling playback features of the dynamic 3D visualization 116*a*. For example, the playback controls 402 may include a play button, which when selected, provides a dynamic display of the plurality of 3D visualizations 116 of the morph-able 3D model 304 corresponding to measurements acquired of the patient's airway.

FIG. 4B illustrates an example transformation of the morph-able 3D model 304. For example, in response to receiving an instruction to play/playback the dynamic 3D visualization 125, a plurality of 3D visualizations 116*b-n* of the morph-able 3D model 304 may be displayed in succession. In the example second 3D visualization 116*b*, the morph-able 3D model 304 represented in the first 3D visualization 116*a* may be updated to represent changes to the patient's airway based on updated measurements of the airway included in additional acoustic measurement data 114 received by the READ system 110. In some examples, the color of at least a portion of the morph-able 3D model 304 may be altered to show the measurement changes. In some examples, the GUI 124 may further include a display of data 404. For example, the data 404 may include measurement data (e.g., volume and area measurements) associated with the patient's upper airway.

FIG. 4C includes a third 3D visualization 116*c* illustrating another example transformation of the morph-able 3D model 304 as part of the dynamic 3D visualization 125. For example the morph-able 3D model 304 represented in the second 3D visualization 116*b* may be updated to represent changes to the patient's airway based on updated measurements of the airway included in additional acoustic measurement data 114 received by the READ system 110.

FIG. 4D shows an example rotation of the third 3D visualization 116*c* showing another perspective of the morph-able 3D model 304. The rotation of the morph-able 3D model 304 may be performed automatically, or the model may be rotated on the display screen 104 responsive to a user input. In some examples, such as if the user is wearing 3D goggles, the user may be able to rotate the view of the morph-able 3D model 304 by turning their head. For example, by rotating the visualization 116*c*, the user may be enabled to visually observe movements of and changes to various parts of the patient's airway anatomy from various perspectives. In some examples, the GUI 124 may include functionality controls that enable the user to rotate, zoom in/out, or otherwise manipulate the display of the morph-able 3D model 304. In other examples, the user may be enabled to manipulate the display of the morph-able 3D model 304 by selecting the 3D visualization 116 of the morph-able 3D model 304 and moving a cursor.

FIG. 4E shows another example rotation of the third 3D visualization 116*c* (performed automatically, or the model may be rotated on the display screen 104 responsive to a user input) showing another perspective of the morph-able 3D model 304.

FIG. 4F includes a fourth 3D visualization 116*d* illustrating another example transformation of the morph-able 3D model 304 as part of the dynamic 3D visualization 125. For example, in a fourth visualization 116*d*, the morph-able 3D model 304 is rotated based on the rotation shown in FIG. 4E and updated to represent changes to the patient's airway based updated measurements of the airway included in additional acoustic measurement data 114 received by the READ system 110.

FIG. 4G shows another example rotation of the third 3D visualization 116*d* (performed automatically, or the model may be rotated on the display screen 104 responsive to a user input) showing another perspective of the morph-able 3D model 304.

FIG. 4H includes a fifth 3D visualization 116*e* illustrating another example transformation of the morph-able 3D model 304 as part of the dynamic 3D visualization 125. For example, in a fifth visualization 116*e*, the morph-able 3D model 304 is rotated based on the rotation shown in FIG. 4G and updated to represent changes to the patient's airway based updated measurements of the airway included in additional acoustic measurement data 114 received by the READ system 110.

FIG. 4I shows another example rotation of the fifth 3D visualization 116e (performed automatically, or the model may be rotated on the display screen 104 responsive to a user input) showing another perspective of the morph-able 3D model 304.

FIG. 4J includes a sixth 3D visualization 116f illustrating another example transformation of the morph-able 3D model 304 as part of the dynamic 3D visualization 125. For example, in a sixth visualization 116f, the morph-able 3D model 304 is rotated based on the rotation shown in FIG. 4I and updated to represent changes to the patient's airway based updated measurements of the airway included in additional acoustic measurement data 114 received by the READ system 110.

FIG. 4K shows another example rotation of the sixth 3D visualization 116f (performed automatically, or the model may be rotated on the display screen 104 responsive to a user input) showing another perspective of the morph-able 3D model 304.

FIG. 4L includes a seventh 3D visualization 116g illustrating another example transformation of the morph-able 3D model 304 as part of the dynamic 3D visualization 125. For example, in a seventh visualization 116g, the morph-able 3D model 304 is rotated based on the rotation shown in FIG. 4K and updated to represent changes to the patient's airway based updated measurements of the airway included in additional acoustic measurement data 114 received by the READ system 110.

FIG. 4M shows another example rotation of the seventh 3D visualization 116g (performed automatically, or the model may be rotated on the display screen 104 responsive to a user input) showing another perspective of the morph-able 3D model 304.

FIG. 4N shows the seventh 3D visualization 116g further rotated and showing another perspective of the morph-able 3D model 304.

FIG. 4O includes an eighth 3D visualization 116h illustrating another example transformation of the morph-able 3D model 304 as part of the dynamic 3D visualization 125. For example, in the eighth visualization 116h, the morph-able 3D model 304 is rotated based on the rotation shown in FIG. 4K and updated to represent changes to the patient's airway based updated measurements of the airway included in additional acoustic measurement data 114 received by the READ system 110.

FIG. 4P illustrates an example visualization 116 of a morph-able 3D model 304 generated by aspects of the present disclosure, wherein portions of the model may be colorized to represent certain measurements and/or changes to the measurements of the airway according to received acoustic measurement data 114. For example, colorization may be utilized to represent various tissue thicknesses. In some examples, a colorization scale 406 may be provided.

Figure 5:
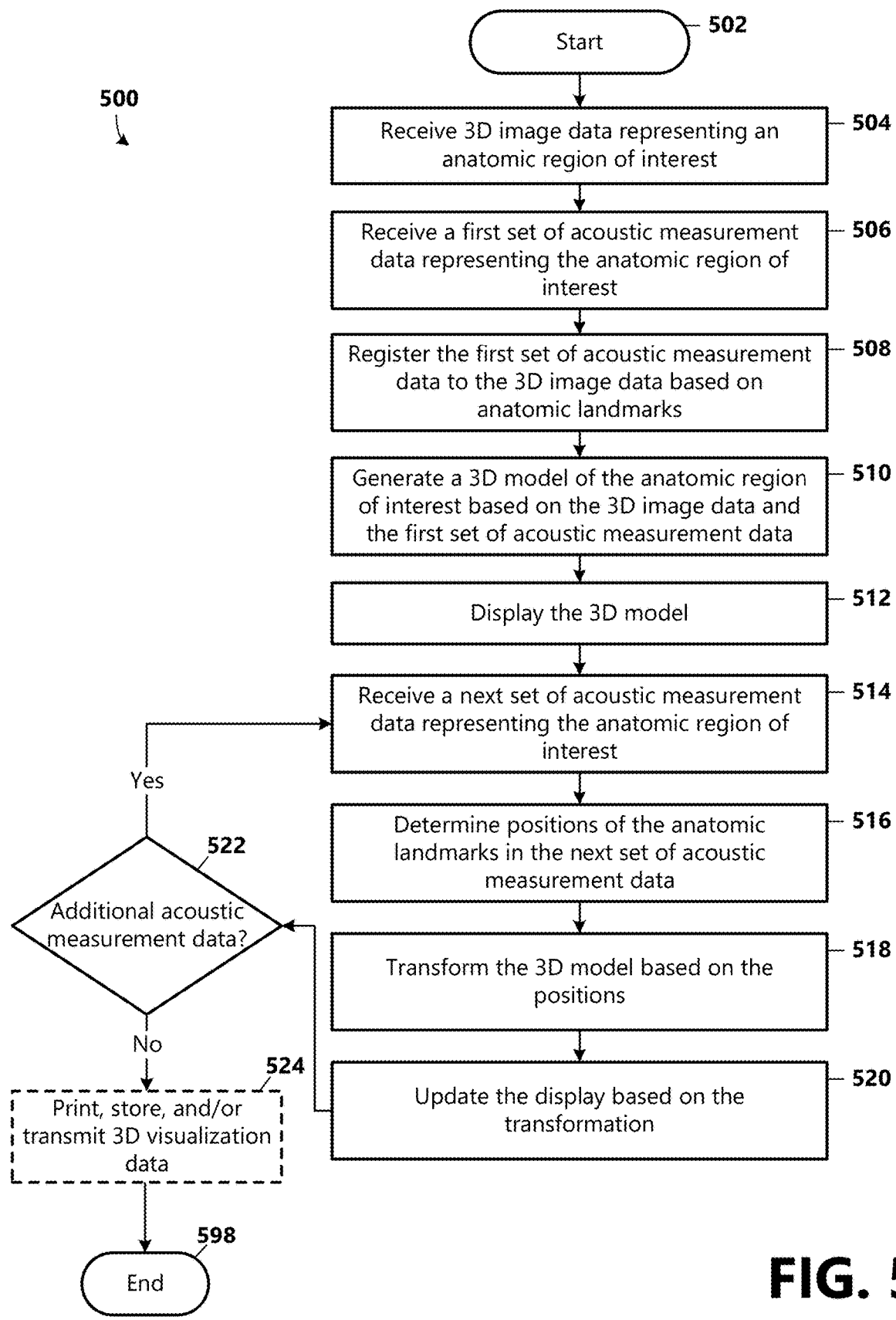
FIG. 5 is a flow diagram depicting general stages of an example process for providing a 3D visual representation of an anatomic region of interest that may be dynamically transformed to characterize the movements of and/or changes to the region of interest.

FIG. 5 is a flow diagram depicting general stages of an example process for generating and providing 3D visual representations 116 of an anatomic region of interest that may be dynamically transformed in relation to movements of and/or changes to the region of interest. With reference now to FIG. 5, the method 500 starts at OPERATION 502 and proceeds to OPERATION 504, where the READ system 110 receives static 3D image data 112 representing upper airway anatomy image information obtained from the static 3D imaging device 106 (e.g., CBCT device). As described above, the static 3D image data 112 may include visualizations (e.g., sagittal, axial, coronal, and 3D views), measurements (e.g., volume and area measurements), and visual graphs of the patient's upper airway anatomy.

At OPERATION 506, the READ system 110 receives the first set of acoustic measurement data 114 representing upper airway anatomy image information obtained from the acoustic reflection measurement device 108 (e.g., a Pharyngometer® and Rhinometer). The static 3D image data 112 (first set of image data) and the first set of acoustic measurement data 114 at least in part represent common upper airway anatomy of the patient. The acoustic measurement data 114 may include calculations of the cross-sectional areas (CSA), length, and volume of the upper airway of the patient. These acoustic measurement data 114 may be represented as 2D line graphs depicting the cross-sectional area of the airway as a function of distance.

At OPERATION 508, the READ system 110 registers the first set of acoustic measurement data 114 to the static 3D image data 112 based on identified anatomic landmarks 302.

At OPERATION 510, the READ system 110 generates a 3D model 304 of the anatomic region of interest based on the static 3D image data 112 and the first set of acoustic measurement data 114 and the identified anatomic landmarks 302, wherein the 3D model 304 includes mappings of the anatomic landmarks between the static 3D image data 112 and the acoustic measurement data 114.

At OPERATION 512, the READ system 110 displays the 3D model 304 on the display screen 104.

At OPERATION 514, the READ system 110 receives a next/additional set of acoustic measurement data 114 representing the anatomic region of interest. The next set of acoustic measurement data 114 may include one or more acoustic measurements, for example, representing a change or a sequence of changes to the anatomic region of interest. According to an example, the changes to the anatomic region of interest may be responsive to mandibular repositioning, breathing activity, the patient performing a Müller's maneuver or a modified Müller's maneuver, etc.

At OPERATION 516, the READ system 110 determines positions and measurements of the anatomic landmarks 302 in the next set of acoustic measurement data 114 and maps the positions and measurements to the corresponding anatomic landmarks 302 in the 3D model 304.

At OPERATION 518, the READ system 110 transforms the 3D model 304 based on the positions and measurements of the anatomic landmarks 302 included in the additional set of acoustic measurement data 114.

At OPERATION 520, the READ system 110 updates the graphical display of the 3D model 304 based on the transformation, thus providing a dynamic 3D visualization 125 of the anatomic region of interest. As part of updating the graphical display of the 3D model 304, the READ system 110 may colorize the 3D model 304 or portions of the 3D model representative of the updated positions and measurements to the patient's airway.

At DECISION OPERATION 522, a determination may be made as to whether additional acoustic measurement data 114 are provided to the READ system 110. If additional acoustic measure data 114 are provided, the method 500 may return to OPERATION 514; else, the method 500 may proceed to OPTIONAL OPERATION 524 where, in response to a request to print, store, or transmit data received and/or determined by the READ system 110, the system may output the requested data to a printer, store the data on a data storage device, or use an email application or other delivery mechanism to transmit the data to another computing device. The method 500 may end at OPERATION 598.

Figure 6:
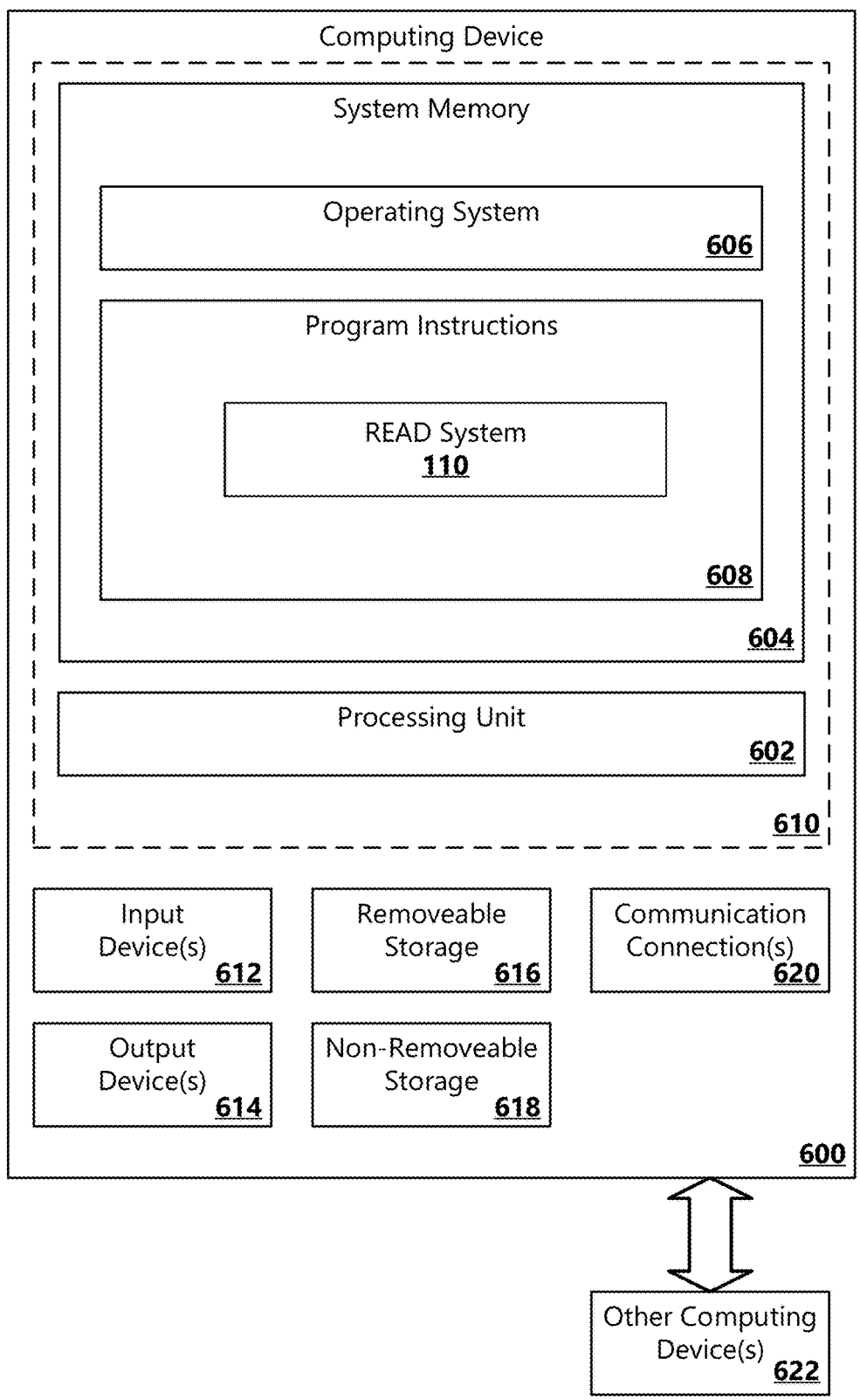
FIG. 6 is a block diagram illustrating example physical components of a computing device or system with which embodiments may be practiced.

FIG. 6 is a block diagram illustrating physical components of an example computing device with which aspects may be practiced. The computing device 600 may include at least one processing unit 602 and a system memory 604. The system memory 604 may comprise, but is not limited to, volatile (e.g. random access memory (RAM)), non-volatile (e.g. read-only memory (ROM)), flash memory, or any combination thereof. System memory 604 may include operating system 606, one or more program instructions 608, and may include sufficient computer-executable instructions for the READ system 110, which when executed, perform functionalities as described herein. Operating system 606, for example, may be suitable for controlling the operation of computing device 600. Furthermore, aspects may be practiced in conjunction with a graphics library, other operating systems, or any other application program and is not limited to any particular application or system. This basic configuration is illustrated by those components within a dashed line 610. Computing device 600 may also include one or more input device(s) 612 (keyboard, mouse, pen, touch input device, etc.) and one or more output device(s) 614 (e.g., display, speakers, a printer, etc.).

The computing device 600 may also include additional data storage devices (removable or non-removable) such as, for example, magnetic disks, optical disks, or tape. Such additional storage is illustrated by a removable storage 616 and a non-removable storage 618. Computing device 600 may also contain a communication connection 620 that may allow computing device 600 to communicate with other computing devices 622, such as over a network in a distributed computing environment, for example, an intranet or the Internet. Communication connection 620 is one example of a communication medium, via which computer-readable transmission media (i.e., signals) may be propagated.

Programming modules may include routines, programs, components, data structures, and other types of structures that may perform particular tasks or that may implement particular abstract data types. Moreover, aspects may be practiced with other computer system configurations, including hand-held devices, multiprocessor systems, microprocessor-based or programmable user electronics, minicomputers, mainframe computers, and the like. Aspects may also be practiced in distributed computing environments where tasks are performed by remote processing devices that are linked through a communications network. In a distributed computing environment, programming modules may be located in both local and remote memory storage devices.

Furthermore, aspects may be practiced in an electrical circuit comprising discrete electronic elements, packaged or integrated electronic chips containing logic gates, a circuit using a microprocessor, or on a single chip containing electronic elements or microprocessors (e.g., a system-on-a-chip (SoC)). Aspects may also be practiced using other technologies capable of performing logical operations such as, for example, AND, OR, and NOT, including, but not limited to, mechanical, optical, fluidic, and quantum technologies. In addition, aspects may be practiced within a general purpose computer or in any other circuits or systems.

Aspects may be implemented as a computer process (method), a computing system, or as an article of manufacture, such as a computer program product or computer-readable storage medium. The computer program product may be a computer storage medium readable by a computer system and encoding a computer program of instructions for executing a computer process. Accordingly, hardware or software (including firmware, resident software, microcode, etc.) may provide aspects discussed herein. Aspects may take the form of a computer program product on a computer-usable or computer-readable storage medium having computer-usable or computer-readable program code embodied in the medium for use by, or in connection with, an instruction execution system.

Although aspects have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data or computer-executable instructions readable by a computing device. The term computer-readable storage media does not include computer-readable transmission media.

Aspects of the present invention may be used in various distributed computing environments where tasks are performed by remote processing devices that are linked through a communications network.

Aspects of the invention may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing device 600 or any other computing devices 622, in combination with computing device 600, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with the described aspects.

The description and illustration of one or more aspects provided in this application are intended to provide a thorough and complete disclosure of the full scope of the subject matter to those skilled in the art and are not intended to limit or restrict the scope of the invention as claimed in any way. The aspects, examples, and details provided in this application are considered sufficient to convey possession and enable those skilled in the art to practice the best mode of the claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, aspects, example, or detail provided in this application unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept provided in this application that do not depart from the broader scope of the present disclosure.

I claim:

1. A system for providing a dynamic 3D visualization of an airway of an individual, the system comprising:
at least one processor;
a memory storage device including instructions that, when executed by the at least one processor, cause the system to:
receive static 3D image data representing an airway of an individual, wherein the airway comprises one or more anatomic landmarks;
automatically detect the one or more anatomic landmarks in the static 3D image data;
receive, through a graphical user interface, an adjustment to the automatically detected anatomic landmarks in the static 3D image data;
receive a first set of acoustic measurement data representing the airway, wherein the first set of acoustic measurement data comprises a plurality of acoustic measurements of cross-sectional area, length, and volume of the airway at a first time;
automatically detect the one or more anatomic landmarks in the first set of acoustic measurement data;
map the first set of acoustic measurement data to the static 3D image data based on the one or more anatomic landmarks to generate a first 3D visualization of the airway at the first time;
receive a second set of acoustic measurement data representing the airway, wherein the second set of acoustic measurement data comprises a plurality of acoustic measurements of cross-sectional area, length, and volume of the airway at a second time;
retrieve, from a knowledge database and based on the second set of acoustic measurement data, a reference static 3D image;
map the second set of acoustic measurement data to the static 3D image data based on the one or more anatomic landmarks;
transform the first 3D visualization into a second 3D visualization in real time based on the receiving of the second set of acoustic measurements and using the reference static 3D image as a target image;
cause display of a dynamic 3D visualization of the airway from a first perspective between the first time and the second time, wherein the dynamic 3D visualization comprises an animation of a change between at least the first 3D visualization and the second 3D visualization;
store a recording of the dynamic 3D visualization;
receive user input through the graphical user interface to cause playback of the dynamic 3D visualization; and
rotate, based on the user input, a view of the dynamic 3D visualization to display the animation of the change from a second perspective that is different from the first perspective.

2. The system of claim 1, wherein the static 3D image data comprise one or more cone beam computed tomography images.

3. The system of claim 1, wherein the acoustic measurement data comprise acoustic measurements generated by at least one of:
a pharyngometer; and
a rhinometer.

4. The system of claim 1, wherein the one or more anatomic landmarks include a hyoid bone.

5. The system of claim 1, wherein the first set of acoustic measurement data represent the airway of the individual during a baseline recording obtained while the individual performs a modified Müller's maneuver.

6. The system of claim 5, wherein the first set of acoustic measurement data includes an indication, based on barometric air pressure sensor data, that the individual performed a full expulsion of air as part of the modified Müller's maneuver.

7. The system of claim 1, wherein the transforming of the first 3D visualization into the second 3D visualization comprises:
transforming the first 3D visualization based on a ratio of change between the first and second sets of acoustic measurement data.

8. The system of claim 1, wherein:
the first set of acoustic measurement data represents the airway during a baseline recording; and
the second set of acoustic measurement data represents the airway during a mandibular repositioning.

9. The system of claim 8, wherein:
the mandibular repositioning comprises a repositioning of the individual's mandible in a plurality of mandibular translations including at least two of:
a vertical translation;
an anteroposterior translation; and
a lateral translation; and
a rotation around at least one axis including at least one of:
a pitch;
a roll; and
a yaw.

10. The system of claim 1, wherein the second set of acoustic measurement data is included in a continual feed of acoustic measurement data.

11. The system of claim 1, wherein the instructions further cause the system to:
receive additional static 3D image data or static 2D image data representing the airway including the one or more anatomic landmarks;
based on the one or more anatomic landmarks, map the additional static 3D or static 2D image data to the static 3D image data; and
superimpose the additional static 3D or static 2D image data on the static 3D image data and the first set of acoustic measurement data in the dynamic 3D visualization.

12. A method for providing a dynamic 3D visualization of an airway of an individual, comprising:
receiving static 3D image data representing airway, wherein the an airway of the individual comprises one or more anatomic landmarks;
automatically detecting the one or more anatomic landmarks in the static 3D image data;
receiving, through a graphical user interface, an adjustment to the automatically detected anatomic landmarks in the static 3D image data;
receiving a first set of acoustic measurement data representing the airway, wherein the first set of acoustic measurement data comprises a plurality of acoustic measurements of cross-sectional area, length, and volume of the airway at a first time;
automatically detecting the one or more anatomic landmarks in the first set of acoustic measurement data;
mapping the first set of acoustic measurement data to the static 3D image data based on the one or more anatomic landmarks to generate a first 3D visualization of the airway at the first time;

performing a mandibular repositioning on the individual using an oral appliance;

receiving a second set of acoustic measurement data representing the airway, wherein the second set of acoustic measurement data comprises a plurality of acoustic measures of cross-sectional area, length, and volume of the airway at a second time following the mandibular repositioning using the oral appliance;

retrieving, from a knowledge database and based on the second set of acoustic measurement data, a reference static 3D image;

mapping the second set of acoustic measurement data to the static 3D image data based on the one or more anatomic landmarks;

transforming the first 3D visualization into a second 3D visualization in real time based on receiving the second set of acoustic measurements and using the reference static 3D image as a target image;

causing display of a dynamic 3D visualization of the airway from a first perspective between the first time and the second time, wherein the dynamic 3D visualization comprises an animation of a change between at least the first 3D visualization and the second 3D visualization;

storing a recording of the dynamic 3D visualization;

receiving user input through the graphical user interface; and rotating, based on the user input, a view of the dynamic 3D visualization to display the animation of the change from a second perspective that is different from the first perspective.

13. The method of claim 12, wherein:

receiving the first set of acoustic measurement data comprises receiving acoustic measurements representing the individual's airway during a baseline recording;

receiving the second set of acoustic measurement data comprises receiving acoustic measurements representing a change of the individual's airway between the first and second sets of acoustic measurement data; and transforming the first 3D visualization into the second 3D visualization comprises transforming the first 3D visualization based on a ratio of the change.

14. The method of claim 12, wherein receiving the second set of acoustic measurement data comprises receiving a continual feed of acoustic measurement data including the second set of acoustic measurement data.

15. The method of claim 12, further comprising:

receiving additional static 3D image data or static 2D image data representing the airway including the one or more anatomic landmarks;

based on the one or more anatomic landmarks, mapping the additional static 3D or static 2D image data to the static 3D image data; and superimposing the additional static 3D or static 2D image data on the static 3D image data and the first set of acoustic measurement data in the first 3D visualization.

16. A computer readable storage media that includes executable instructions which, when executed by a processor, provide a dynamic 3D visualization of an airway of an individual, the instructions comprising:

receiving static 3D image data representing an airway of an individual, wherein the airway comprises one or more anatomic landmarks;

automatically detecting the one or more anatomic landmarks in the static 3D image data;

receiving, through a graphical user interface, an adjustment to the automatically detected anatomic landmarks in the static 3D image data;

receiving a first set of acoustic measurement data representing the airway, wherein the first set of acoustic measurement data comprises a plurality of acoustic measurements of cross-sectional area, length, and volume of the airway at a first time;

automatically detecting the one or more anatomic landmarks in the first set of acoustic measurement data;

mapping the first set of acoustic measurement data to the static 3D image data based on the one or more anatomic landmarks to generate a first 3D visualization of the airway at the first time;

receiving a continual feed of acoustic measurement data representing the airway, including a second set of acoustic measurement data, wherein the second set of acoustic measurement data comprises a plurality of acoustic measures of cross-sectional area, length, and volume of the airway at a second time;

retrieving, from a knowledge database and based on the second set of acoustic measurement data, a reference static 3D image;

mapping the second set of acoustic measurement data to the static 3D image data based on the one or more anatomic landmarks;

transforming the first 3D visualization into a second 3D visualization in real time based on receiving the continual feed of acoustic measurement data and using the reference static 3D image as a target image;

causing display of a dynamic 3D visualization of the airway from a first perspective between the first time and the second time, wherein the dynamic 3D visualization comprises an animation of a change between at least the first 3D visualization and the second 3D visualization;

storing a recording of the dynamic 3D visualization;

receiving user input through the graphical user interface; and rotating, based on the user input, a view of the dynamic 3D visualization to display the animation of the change from a second perspective that is different from the first perspective.

17. The system of claim 1, wherein the instructions further cause the system to provide playback controls for controlling playback of the display of the dynamic 3D visualization of the airway between the first time and the second time.

18. The method of claim 12, wherein displaying the dynamic 3D visualization of the airway between the first time and the second time shows an animated change in the individual's upper airway during at least one of:

a breath;

mandibular repositioning; and a Müller's maneuver.

* * * * *